US009701983B2

(12) United States Patent
Gomez Sebastian et al.

(10) Patent No.: US 9,701,983 B2
(45) Date of Patent: Jul. 11, 2017

(54) BACULOVIRAL DNA ELEMENTS FOR THE EXPRESSION OF RECOMBINANT PROTEINS IN A HOST INSECT

(75) Inventors: Silvia Gomez Sebastian, Madrid (ES); Javier López Vidal, Madrid (ES); José Angel Martinez Escribano, Madrid (ES)

(73) Assignee: ALTERNATIVE GENE EXPRESSION S.L., Madrid (ES)

(*) Notice: Subject to any disclaimer, the term of this patent is extended or adjusted under 35 U.S.C. 154(b) by 0 days.

(21) Appl. No.: 14/407,709

(22) PCT Filed: Jun. 12, 2012

(86) PCT No.: PCT/EP2012/061088
§ 371 (c)(1),
(2), (4) Date: Apr. 27, 2015

(87) PCT Pub. No.: WO2012/168493
PCT Pub. Date: Dec. 13, 2012

(65) Prior Publication Data
US 2015/0240260 A1 Aug. 27, 2015

(51) Int. Cl.
A01N 63/00 (2006.01)
C12N 15/00 (2006.01)
C12Q 1/68 (2006.01)
C12N 15/86 (2006.01)
A01K 67/033 (2006.01)

(52) U.S. Cl.
CPC .......... *C12N 15/86* (2013.01); *A01K 67/0339* (2013.01); *A01K 2207/05* (2013.01); *A01K 2217/20* (2013.01); *A01K 2227/706* (2013.01); *A01K 2267/01* (2013.01); *C12N 2710/14043* (2013.01); *C12N 2710/14122* (2013.01); *C12N 2830/002* (2013.01); *C12N 2830/205* (2013.01); *C12N 2830/60* (2013.01)

(58) Field of Classification Search
USPC ................................ 424/93.2; 435/6.1, 320.1
See application file for complete search history.

(56) References Cited

U.S. PATENT DOCUMENTS 5,965,393 A 10/1999 Hasnain et al.
2009/0068703 A1 3/2009 Chao et al.

FOREIGN PATENT DOCUMENTS

| EP | 1811027 A1 | 7/2007 |
| ES | 2232308 B1 | 5/2005 |
| KR | 20010074351 A | 8/2001 |
| WO | WO-2005/085456 A1 | 9/2005 |
| WO | WO-2010/025764 A1 | 3/2010 |
| WO | WO-2011/069562 A1 | 6/2011 |
| WO | WO-2012/168492 A2 | 12/2012 |
| WO | WO-2012/168789 A2 | 12/2012 |
| WO | WO-2012/169940 A2 | 12/2012 |

OTHER PUBLICATIONS

Lopez-Vidal et al., Insect-derived promoters for baculovirus vectors improvement. FESS Journal, (Jun. 2011) vol. 278, No. Suppl. 1,Sp. Iss. SI, pp. 438. Meeting Info.: 36th FESS Congress of the Biochemistry for Tomorrows Medicine.Torino, Italy. Jun. 25-30, 2011. Federat Soc Biochem & Mol Biol. ISSN:1742-464X. E-ISSN: 1742-4658.*
Weyer et al A baculovirus dual expression vector derived from the Autographa cal.ifornica nuclear polyhedrosis virus polyhedrin and pIO promoters: co-expression of two influenza virus genes in insect cells Journal of General Virology (1991), 72, 2961-2974.*
Kimchi-Sarfaty Cet al., A "silent" polymorphism in the MDR1 gene changes substrate specificity.Science. Jan. 26, 2007;315(5811):525-8.*
Ngo, in The Protein Folding Problem and Tertiary Structure Prediction, Merz et al. (eds.), Birkhauser Boston: Boston, MA, pp. 433 and 492-495, 1994.*
Voet, Biochemistry John Wiley and Sons, 1990, pp. 126-128.*
Rudinger (in Peptide Hormones, Parsons (ed.), University Park Press: Baltimore, MD, pp. 1-7, 1976.*
Lepidoptera—Wikipedia, the free encyclopedia pp. 1-29, downloaded Aug. 30, 2016.*
Alves, C.A., et al., "*hycu-hr6*, A large homologous region of the *Hypantria cunea* nucleopolyhedrovirus genome, as a powerful and versatile enhancer in insect expression systems", *Virus Genes*, Kluwer Academic Publishers, BO, vol. 39, No. 3, 2009, pp. 403-408.
Baek, J.O., et al., "Production and purification of human papillomavirus type 33 L1 virus-like particles from Spodoptera frugiperda 9 cells using two-step column chromatography", *Protein Expression and Purification*, vol. 75, No. 2, 2010, pp. 211-217.
Berger, I., et al., "Baculovirus expression system for heterologus multiprotein complexes", *Nature Biotechnology*, vol. 22, No. 12, 2004, pp. 1583-1587.
Bieniossek, C., et al.,"MultiBac: expanding the research toolbox for multiprotein complexes", *Trends in Biochemical Sciences*, vol. 37, No. 2, 2012, pp. 49-57.
Crouch, E.A., et al., "Effects of baculovirus transactivators IE-1 and IE-2 on the *Drosophila* heat shock 70 promoter in two insect cell lines", *Archives of Virology; Official Journal of the Virology Division of the International Union of Microbiological Societies*, Springer-Verlag VI, vol. 150, No. 8, 2005, pp. 1563-1578.

(Continued)

Primary Examiner — Maria Leavitt
(74) *Attorney, Agent, or Firm* — McCarter & English, LLP; Danielle L. Herritt; Jill Ann Mello

(57) ABSTRACT

Reagents and methods are provided that allow for an improved expression of a recombinant protein in an insect, More specifically, the introduction of recombinant DNA elements into an insect larva allows for the increased expression of a recombinant protein, an improvement of the correct folding of said protein and an increase in the survival rate after infection of the insect These recombinant DNA elements can be introduced, for example, into insect larvae via a recombinant baculovirus, which has incorporated said elements. The recombinant DNA elements include nucleic acids encoding transcriptional regulators, such as IE-0 and IE-1, transcriptional, enhancer elements, such as the homologous region (hr) and promoters.

6 Claims, 8 Drawing Sheets

(56) References Cited

OTHER PUBLICATIONS

Dai, X., "The acidic activation domains of the baculovirus transactivators IE1 and IE0 are functional for transcriptional activation in both insect and mammalian cells", Journal of General Virology, vol. 85, No. 3, 2004, pp. 573-582.

Fan, H., et al., "Construction and immunogenicity of recombinant pseudotype baculovirus expressing the capsid protein of porcine circovirus type 2 in mice", Journal of Virological Methods, vol. 150, No. 1-2, 2008, pp. 21-26.

Gomez-Casado, E., et al., "Insect larvae biofactories as a platform for influenza vaccine production", Protein Expression and Purification, vol. 79, 2011, pp. 35-43.

Gomi, S., et al., "Sequence analysis of the genome of Bombyx mori nucleopolyhedrovirus", Journal of General Virology, vol. 80, No. 5, 1999, 1323-1337.

Guo, M., et al., "Expression and Self-Assembly in Baculovirus of Porcine Enteric Calicivirus Capsids into Virus-Like Particles and Their Use in an Enzyme-Linked Immunosorbent Assay for Antibody Detection in Swine", Journal of Clinical Microbiology, vol. 39, No. 4, 2001, pp. 1487-1493.

Hashimoto, Y., et al., "Ao38, a new cell line from eggs of the black witch moth, Ascalapha odorata (Lepidoptera: Noctuidae), is permissive for AcMNPV infection and produces high levels of recombinant proteins", BMC Biotechnology, vol. 10, 2010, p. 50.

Hill-Perkins, M.S., et al., "A baculovirus expression vector derived from the basic protein promoter of Autographa californica nuclear polyhedrosis virus", Journal of General Virology, vol. 71, 1990, pp. 971-976.

Hitchman, R.B., et al., "Baculovirus expression systems for recombinant protein production in insect cells", Recent Patents on Biotechnology, vol. 3, No. 1, 2009, pp. 46-54.

International Search Report and Written Opinion of PCT/EP2012/061088, mailed Mar. 6, 2013.

Kang, W., "IE1 and hr facilitate the localization of Bombyx mori nucleopolyhedrovirus ORF8 to specific nuclear sites", Journal of General Virology, vol. 86, No. 11, 2005, pp. 3031-3038.

Kanginakudru, S., et al., "Targeting ie-1 gene by RNAi induces baculoviral resistance in lepidopteran cell lines and in transgenic silkworms", Insect Molecular Biology, vol. 16, No. 5, 2007, pp. 635-644.

Kawasaki, Y., "Analysis of baculovirus IE1 in living cells: dynamics and spatial relationships in viral structural proteins", Journal of General Virology, vol. 85, No. 12, 2004, pp. 3575-3583.

Lin, X., et al., "Baculovirus immediately early 1, a mediator for homologous regions enhancer function in trans", Virology Journal, vol. 7, No. 32, 2010.

Lo, H.-R., et al., "Novel Baculovirus DNA Elements Strongly Stimulate Activities of Exogenous and Endogenous Promoters", Journal of Biological Chemistry, vol. 277, No. 7, 2002, pp. 5256-5264.

López-Vidal, J., et al., "Characterization of a Trichoplusia ni hexamerin-derived promoter in the AcMNPV baculovirus vector", Journal of Biotechnology, vol. 165, No. 3-4, 2013, pp. 201-208.

Majima, K., et al., "Divergence and evolution of homologous regions of Bombyx mori nuclear polyhedrosis virus", Journal of Virology, vol. 67, No. 12, 1993, pp. 7513-7521.

Nagai, S., et al., "Comparative transient expression assay analysis of hycu-hr6- and IE1-dependent regulation of baculovirus gp64 early promoters in three insect cell lines", Virus Research, Amsterdam, NL, vol. 155, No. 1, 2011, pp. 83-90.

Nagamine, T., et al., "Focal Distribution of Baculovirus IE1 Triggered by its Binding to the hr DNA Elements", Journal of Virology, vol. 79, No. 1, 2004, pp. 39-46.

Nagamine, T., et al., "Induction of a sub-nuclear structure by the simultaneous expression of baculovirus proteins, IE1, LEF3, and P143 in the presence of hr", Virology, Academic Press, Orlando, US, vol. 352, No. 2, 2006, pp. 400-407.

Nettleship, J.E., et al., "Recent advances in the production of proteins in insect and mammalian cells for structural biology", Journal of Structural Biology, Academic Press, US, vol. 172, No. 1, 2010, pp. 55-65.

Ogawa, S., et al., "Generation of a transgenic silkworm that secretes recombinant proteins in the sericin layer of cocoon: Production of recombinant human serum albumin", Journal of Biotechnology, Elsevier Science Publishers, vol. 128, No. 3, 2007, pp. 531-544.

Okano, L., et al., "Colocalization of baculovirus IE-1 and two DNA-binding proteins, DBF and LEF-3, to viral replication factories", Journal of Virology, vol. 73, No. 1, 1999, pp. 110-119.

Olson, V.A., et al., "The highly conserved basic domain I of baculovirus IE1 is required for hr enhancer DNA binding and hr-dependent transactivation", Journal of Virology, The American Society for Microbiology, US, vol. 77, No. 10, 2003, pp. 5668-5677.

Passarelli, A.L., et al., "Three baculovirus genes involved in late and very late gene expression: ie-1, ie-n, and lef-2", Journal of Virology, vol. 67, No. 4, 1993, pp. 2149-2158.

Perez-Filgueira, D.M., et al., "Development of a low-cost, insect larvae-derived recombinant subunit vaccine against RHDV", Virology, vol. 364, No. 2, 2007, pp. 422-430.

Radner, S., et al., "Transient transfection couples to baculovirus infection for rapid protein expression screening in insect cells", Journal of Structural Biology, vol. 179, No. 1, 2012, pp. 46-55.

Rodems, S. M., et al., "DNA-dependent transregulation by IE1 of Autographa californica nuclear polyhedrosis virus: IE1 domains required for transactivation and DNA binding", Journal of Virology, vol. 71, 1997, pp. 9270-9277.

Senger, T., et al., "Enhanced papillomavirus-like particle production in insect cells", Virology, vol. 388, No. 2, 2009, pp. 344-353.

Smith, G.E., et al., "Production of human beta interferon in insect cells infected with a baculovirus expression vector", Molecular Cellular Biology, vol. 3, 1983, pp. 2156-2165.

Taticek, R.A., el al., "Comparison of growth and recombinant protein expression in two different insect cells lines in attached and suspension culture", Biotechnology Progress, vol. 17, No. 4, 2001, pp. 676-684.

Tomita, M., et al., "A germline transgenic silkworm that secretes recombinant proteins in the sericin layer of cocoon", Transgenic Research, Kluwer Academic Publishers-Plenum Publishers, vol. 16, No. 4, 2007, pp. 449-465.

Valdes, V.J., et al., "Using double-stranded RNA to prevent in vitro and in vivo viral infections by recombinant baculovirus", Journal of Biological Chemistry, vol. 278, No. 21, 2003, pp. 19317-19324.

Venkaiah, B., et al., "An additional copy of the homologous region (hrl) sequence in the Autographa californica multinucleocapsid polyhedrosis virus genome promote hyperexpression of foreign genes," Biochemistry, vol. 43, No. 25, 2004, pp. 8143-8151.

International Search Report and Written Opinion of PCT/EP2012/061081, mailed Feb. 19, 2013.

International Search Report and Written Opinion of PCT/EP2013/075812, mailed Apr. 25, 2014.

Guarino, L.A., et al., "Interspersed Homologous DNA of Autographa califomica Nuclear Polyhedrosis Virus Enhances Delayed-Early Gene Expression", Journal of Virology, vol. 60, No. 1, 1986, pp. 215-223.

Gomez-Sebastien, S. et al., "Significant Productivity Improvement of the Baculovirus Expression Vector System by Engineering a Novel Expression Cassette", PLOS One, vol. 9, No. 5, e96562, May 2014, 10 pages.

Knebel, D., et al., "The promoter of the late p10 gene in the insect nuclear polyhedrosis virus Autographa californica: activation by viral gene products and sensitivity to DNA methylation", The EMBO Journal, vol. 4, No. 5, 1985, pp. 1301-1306.

Prikhod'ko, E., et al., "Induction of Apoptosis by Baculovirus Transactivator IE1", Journal of Virology, vol. 70, No. 10, 1996, pp. 7116-7124.

* cited by examiner

Figure 6

SEQUENCE LISTING

```
<160> NUMBER OF SEQ ID NOS: 29

<210> SEQ ID NO 1

<400> SEQUENCE: 1

000

<210> SEQ ID NO 2
<211> LENGTH: 1749
<212> TYPE: DNA
<213> ORGANISM: Autographa californica nucleopolyhedrovirus

<400> SEQUENCE: 2
atgactcaaa tcaacttcaa cgcttcctac acctctgcca gcactccctc tcgtgctagc      60
ttcgacaact catactcgga gttctgcgac aagcaaccta acgattactt gtcttactac     120
aaccacccaa ccccggacgg agctgatact gtcatctccg actctgaaac cgctgccgct     180
```

```
agcaacttcc tcgcctcagt taactcgctc actgacaacg atttggtgga gtgtctgctc    240
aagaccactg acaacctgga ggaagctgtg tcctctgcct actacagcga gtcactcgaa    300
cagccagtgg tcgaacaacc ctctcctagc tcagcttacc acgccgagtc cttcgaacac    360
tctgctggtg tcaaccagcc gtcggccaca ggcaccaaga ggaagttgga cgagtacctg    420
gataactccc agggagttgt gggtcaattc aacaagatca agttgagacc taagtacaag    480
aagagcacca tccagtcatg cgctacactg aacaaaacca tcaaccacaa cactaacatc    540
tgtacagtgg cttccaccca ggagatcact cactacttca caaacgactt cgccccctac    600
ctgatgaggt tcgacgataa cgactacaac tcgaacagat tctccgatca catgtctgaa    660
accggttact acatgttcgt cgttaagaag tccgaggtga agcctttcga aatcatcttc    720
gccaagtacg tctctaacgt ggtctacgag tacacaaaca actactacat ggttgacaac    780
cgtgtgttcg ttgtgaccct cgataagatc cgcttcatga tcagctacaa cctggttaag    840
gagactggca tcgaaatccc acactcacag gacgtctgca acgatgagac cgccgctcaa    900
aactgcaaga agtgtcactt cgtggacgtc caccacacat tcaaggccgc tctgacctcc    960
tacttcaacc tcgatatgta ctacgctcag acaaccttcg tgaccttgct gcaatcactc   1020
ggcgagcgta agtgtggatt cctcttgtcg aagttgtacg agatgtacca ggacaagaac   1080
ctcttcactt tgcccatcat gctgagccgc aaggaatcaa acgagatcga aaccgcctct   1140
aacaacttct tcgtctcgcc atacgtttcc cagatcctca agtactcgga gtccgtccaa   1200
ttcccggaca accctcccaa caagtacgtc gttgataacc tgaacctcat cgtgaacaag   1260
aagagcactc tgacatacaa gtactcgtcc gtcgctaacc tgctcttcaa caactacaag   1320
taccacgaca acatcgcttc taacaacaac gccgagaacc tcaagaaggt caagaaggaa   1380
gacggaagca tgcacatcgt tgagcagtac ttgactcaaa acgtcgataa cgttaagggt   1440
cacaacttca tcgtgttgtc cttcaagaac gaggaaaggc tgaccatcgc taagaagaac   1500
aaggagttct actggatctc tggcgaaatc aaggacgttg atgtgagcca ggtcatccaa   1560
aagtacaaca gattcaagca ccacatgttc gtgatcggca aggtcaaccg tcgcgagtca   1620
actacactgc acaacaactt gctgaagctc ttggccttga tcctgcaggg actggtgcca   1680
ctctccgacg ccatcacatt cgccgagcaa aagctcaact gcaagtacaa gaagttcgag   1740
ttcaactaa                                                            1749

<210> SEQ ID NO 3
<211> LENGTH: 1911
<212> TYPE: DNA
<213> ORGANISM: Autographa californica nucleopolyhedrovirus

<400> SEQUENCE: 3
atgatccgta catccagcca cgtcctgaac gtccaagaaa acatcatgac ttccaactgt     60
gcttccagcc cctactcctg tgaggccact tcagcctgcg ctgaggccca gcaactgcag    120
gtggacacag gtggcgataa gatcgtgaac aaccaggtca ccatgactca aatcaacttc    180
aacgcttcct acacctctgc cagcactccc tctcgtgcta gcttcgacaa ctcatactcg    240
gagttctgcg acaagcaacc taacgattac ttgtcttact acaaccaccc aaccccggac    300
ggagctgata ctgtcatctc cgactctgaa accgctgccg ctagcaactt cctcgcctca    360
gttaactcgc tcactgacaa cgatttggtg gagtgtctgc tcaagaccac tgacaacctg    420
gaggaagctg tgtcctctgc ctactacagc gagtcactcg aacagccagt ggtcgaacaa    480
```

```
cccteteeta getcagetta ccacgccgag teettcgaac acteigcigg tgtcaaccag    540
ccgtcggcca caggcaccaa gaggaagttg gacgagtacc tggataactc ccagggagtt    600
gtgggtcaat tcaacaagat caagttgaga cctaagtaca agaagagcac catccagtca    660
tgcgctacac tggaacaaac catcaaccac aacactaaca tctgtacagt ggcttccacc    720
caggagatca ctcactactt cacaaacgac ttcgcccccct acctgatgag gttcgacgat    780
aacgactaca actcgaacag attctccgat catgtctg aaaccggtta ctacatgttc    840
gtcgttaaga agtccgaggt gaagcctttc gaaatcatct tcgccaagta cgtctctaac    900
gtggtctacg agtacacaaa caactactac atggttgaca accgtgtgtt cgttgtgacc    960
ttcgataaga tccgcttcat gatcagctac aacctggtta aggagactgg catcgaaatc   1020
ccacactcac aggacgtctg caacgatgag accgccgctc aaaactgcaa gaagtgtcac   1080
ttcgtggacg tccaccacac attcaaggcc gctctgacct cctacttcaa cctcgatatg   1140
tactacgctc agacaacctt cgtgaccttg ctgcaatcac tcggcgagcg taagtgtgga   1200
ttcctcttgt cgaagttgta cgagatgtac caggacaaga acctcttcac tttgcccatc   1260
atgctgagcc gcaaggaatc aaacgagatc gaaaccgcct ctaacaactt cttcgtctcg   1320
ccatacgttt cccagatcct caagtactcg gagtccgtcc aattcccgga caaccctccc   1380
aacaagtacg tcgttgataa cctgaacctc atcgtgaaca agaagagcac tctgacatac   1440
aagtactcgt ccgtcgctaa cctgctcttc aacaactaca agtaccacga caacatcgct   1500
tctaacaaca cgccgagaa cctcaagaag gtcaagaagg aagacggaag catgcacatc   1560
gttgagcagt acttgactca aaacgtcgat aacgttaagg gtcacaactt catcgtgttg   1620
tccttcaaga acgaggaaag gctgaccatc gctaagaaga caaggagtt ctactggatc   1680
tctggcgaaa tcaaggacgt tgatgtgagc caggtcatcc aaaagtacaa cagattcaag   1740
caccacatgt tcgtgatcgg caaggtcaac cgtcgcgagt caactacact gcacaacaac   1800
ttgctgaagc tcttggcctt gatcctgcag ggactggtgc cactctccga cgccatcaca   1860
ttcgccgagc aaaagctcaa ctgcaagtac aagaagttcg agttcaacta a             1911

<210> SEQ ID NO 4
<211> LENGTH: 666
<212> TYPE: DNA
<213> ORGANISM: Autographa californica nucleopolyhedrovirus

<400> SEQUENCE: 4
atgactcaaa tcaacttcaa cgcttcctac acctctgcca gcactcctc tcgtgctagc      60
ttcgacaact catactcgga gttctgcgac aagcaaccta acgattactt gtcttactac     120
aaccacccaa cccggacgg agctgatact gtcatctccg actctgaaac cgctgccgct     180
agcaacttcc tcgcctcagt taactcgctc actgacaacg atttggtgga gtgtctgctc     240
aagaccactg acaacctgga ggaagctgtg tcctctgcct actacagcga gtcactcgaa     300
cagccagtgg tcgaacaacc ctctcctagc tcagcttacc gcgccgagtc cttcgaacac     360
tctgctggtg tcaaccagcc gtcggccaca ggcaccaaga ggaagttgga cgagtacctg     420
gataactccc agggagttgt gggtcaattc aacaagatca agttgagacc taagtacaag     480
aagagcacca tccagtcatg cgctacactg gaacaaacca tcaaccacaa cactaacatc     540
tgtacagtgg cttccaccca ggagatcact cactacttca aaacgactt cgcccccctac     600
ctgatgaggt tcgacgataa cgactacaac tcgaacagat tctccgatca catgtctgaa     660
accggt                                                                666
```

<210> SEQ ID NO 5
<211> LENGTH: 828
<212> TYPE: DNA
<213> ORGANISM: Autographa californica nucleopolyhedrovirus

<400> SEQUENCE: 5

```
atgatccgta catccagcca cgtcctgaac gtccaagaaa acatcatgac ttccaactgt      60
gcttccagcc cctactcctg tgaggccact tcagcctgcg ctgaggccca gcaactgcag     120
gtggacacag gtggcgataa gatcgtgaac aaccaggtca ccatgactca aatcaacttc     180
aacgcttcct acacctctgc cagcactccc tctcgtgcta gcttcgacaa ctcatactcg     240
gagttctgcg acaagcaacc taacgattac ttgtcttact acaaccaccc aaccccggac     300
ggagctgata ctgtcatctc cgactctgaa accgctgccg ctagcaactt cctcgcctca     360
gttaactcgc tcactgacaa cgatttggtg gagtgtctgc tcaagaccac tgacaacctg     420
gaggaagctg tgtcctctgc ctactacagc gagtcactcg aacagccagt ggtcgaacaa     480
ccctctccta gctcagctta ccacgccgag tccttcgaac actctgctgg tgtcaaccag     540
ccgtcggcca caggcaccaa gaggaagttg gacgagtacc tggataactc ccagggagtt     600
gtgggtcaat tcaacaagat caagttgaga cctaagtaca agaagagcac catccagtca     660
tgcgctacac tggaacaaac catcaaccac aacactaaca tctgtacagt ggcttccacc     720
caggagatca ctcactactt cacaaacgac ttcgccccct acctgatgag gttcgacgat     780
aacgactaca actcgaacag attctccgat cacatgtctg aaaccggt                  828
```

<210> SEQ ID NO 6
<211> LENGTH: 582
<212> TYPE: PRT
<213> ORGANISM: Autographa californica nucleopolyhedrovirus

<400> SEQUENCE: 6

Met Thr Gln Ile Asn Phe Asn Ala Ser Tyr Thr Ser Ala Ser Thr Pro
1               5                   10                  15

Ser Arg Ala Ser Phe Asp Asn Ser Tyr Ser Glu Phe Cys Asp Lys Gln
            20                  25                  30

Pro Asn Asp Tyr Leu Ser Tyr Tyr Asn His Pro Thr Pro Asp Gly Ala
        35                  40                  45

Asp Thr Val Ile Ser Asp Ser Glu Thr Ala Ala Ser Asn Phe Leu
    50                  55                  60

Ala Ser Val Asn Ser Leu Thr Asp Asn Asp Leu Val Glu Cys Leu Leu
65                  70                  75                  80

Lys Thr Thr Asp Asn Leu Glu Glu Ala Val Ser Ser Ala Tyr Tyr Ser
                85                  90                  95

Glu Ser Leu Glu Gln Pro Val Val Glu Gln Pro Ser Pro Ser Ser Ala
            100                 105                 110

Tyr His Ala Glu Ser Phe Glu His Ser Ala Gly Val Asn Gln Pro Ser
        115                 120                 125

Ala Thr Gly Thr Lys Arg Lys Leu Asp Glu Tyr Leu Asp Asn Ser Gln
    130                 135                 140

Gly Val Val Gly Gln Phe Asn Lys Ile Lys Leu Arg Pro Lys Tyr Lys
145                 150                 155                 160

Lys Ser Thr Ile Gln Ser Cys Ala Thr Leu Glu Gln Thr Ile Asn His
                165                 170                 175

Asn Thr Asn Ile Cys Thr Val Ala Ser Thr Gln Glu Ile Thr His Tyr 180                 185                 190
Phe Thr Asn Asp Phe Ala Pro Tyr Leu Met Arg Phe Asp Asp Asn Asp
              195                 200                 205
Tyr Asn Ser Asn Arg Phe Ser Asp His Met Ser Glu Thr Gly Tyr Tyr
  210                 215                 220
Met Phe Val Val Lys Ser Glu Val Lys Pro Phe Glu Ile Ile Phe
225                 230                 235                 240
Ala Lys Tyr Val Ser Asn Val Val Tyr Glu Tyr Thr Asn Asn Tyr Tyr
              245                 250                 255
Met Val Asp Asn Arg Val Phe Val Val Thr Phe Asp Lys Ile Arg Phe
          260                 265                 270
Met Ile Ser Tyr Asn Leu Val Lys Glu Thr Gly Ile Glu Ile Pro His
      275                 280                 285
Ser Gln Asp Val Cys Asn Asp Glu Thr Ala Ala Gln Asn Cys Lys Lys
  290                 295                 300
Cys His Phe Val Asp Val His His Thr Phe Lys Ala Ala Leu Thr Ser
305                 310                 315                 320
Tyr Phe Asn Leu Asp Met Tyr Tyr Ala Gln Thr Thr Phe Val Thr Leu
              325                 330                 335
Leu Gln Ser Leu Gly Glu Arg Lys Cys Gly Phe Leu Leu Ser Lys Leu
          340                 345                 350
Tyr Glu Met Tyr Gln Asp Lys Asn Leu Phe Thr Leu Pro Ile Met Leu
      355                 360                 365
Ser Arg Lys Glu Ser Asn Glu Ile Glu Thr Ala Ser Asn Asn Phe Phe
  370                 375                 380
Val Ser Pro Tyr Val Ser Gln Ile Leu Lys Tyr Ser Glu Ser Val Gln
385                 390                 395                 400
Phe Pro Asp Asn Pro Pro Asn Lys Tyr Val Val Asp Asn Leu Asn Leu
              405                 410                 415
Ile Val Asn Lys Lys Ser Thr Leu Thr Tyr Lys Tyr Ser Ser Val Ala
          420                 425                 430
Asn Leu Leu Phe Asn Asn Tyr Lys Tyr His Asp Asn Ile Ala Ser Asn
      435                 440                 445
Asn Asn Ala Glu Asn Leu Lys Lys Val Lys Lys Glu Asp Gly Ser Met
  450                 455                 460
His Ile Val Glu Gln Tyr Leu Thr Gln Asn Val Asp Asn Val Lys Gly
465                 470                 475                 480
His Asn Phe Ile Val Leu Ser Phe Lys Asn Glu Glu Arg Leu Thr Ile
              485                 490                 495
Ala Lys Lys Asn Lys Glu Phe Tyr Trp Ile Ser Gly Glu Ile Lys Asp
          500                 505                 510
Val Asp Val Ser Gln Val Ile Gln Lys Tyr Asn Arg Phe Lys His His
      515                 520                 525
Met Phe Val Ile Gly Lys Val Asn Arg Arg Glu Ser Thr Thr Leu His
  530                 535                 540
Asn Asn Leu Leu Lys Leu Leu Ala Leu Ile Leu Gln Gly Leu Val Pro
545                 550                 555                 560
Leu Ser Asp Ala Ile Thr Phe Ala Glu Gln Lys Leu Asn Cys Lys Tyr
              565                 570                 575
Lys Lys Phe Glu Phe Asn
          580

<210> SEQ ID NO 7

<211> LENGTH: 636
<212> TYPE: PRT
<213> ORGANISM: Autographa californica nucleopolyhedrovirus

<400> SEQUENCE: 7

```
Met Ile Arg Thr Ser Ser His Val Leu Asn Val Gln Glu Asn Ile Met
1               5                   10                  15

Thr Ser Asn Cys Ala Ser Ser Pro Tyr Ser Cys Glu Ala Thr Ser Ala
            20                  25                  30

Cys Ala Glu Ala Gln Gln Leu Gln Val Asp Thr Gly Gly Asp Lys Ile
        35                  40                  45

Val Asn Asn Gln Val Thr Met Thr Gln Ile Asn Phe Asn Ala Ser Tyr
    50                  55                  60

Thr Ser Ala Ser Thr Pro Ser Arg Ala Ser Phe Asp Asn Ser Tyr Ser
65                  70                  75                  80

Glu Phe Cys Asp Lys Gln Pro Asn Asp Tyr Leu Ser Tyr Tyr Asn His
                85                  90                  95

Pro Thr Pro Asp Gly Ala Asp Thr Val Ile Ser Asp Ser Glu Thr Ala
            100                 105                 110

Ala Ala Ser Asn Phe Leu Ala Ser Val Asn Ser Leu Thr Asp Asn Asp
        115                 120                 125

Leu Val Glu Cys Leu Leu Lys Thr Thr Asp Asn Leu Glu Glu Ala Val
    130                 135                 140

Ser Ser Ala Tyr Tyr Ser Glu Ser Leu Glu Gln Pro Val Val Glu Gln
145                 150                 155                 160

Pro Ser Pro Ser Ser Ala Tyr His Ala Glu Ser Phe Glu His Ser Ala
                165                 170                 175

Gly Val Asn Gln Pro Ser Ala Thr Gly Thr Lys Arg Lys Leu Asp Glu
            180                 185                 190

Tyr Leu Asp Asn Ser Gln Gly Val Val Gly Gln Phe Asn Lys Ile Lys
        195                 200                 205

Leu Arg Pro Lys Tyr Lys Lys Ser Thr Ile Gln Ser Cys Ala Thr Leu
    210                 215                 220

Glu Gln Thr Ile Asn His Asn Thr Asn Ile Cys Thr Val Ala Ser Thr
225                 230                 235                 240

Gln Glu Ile Thr His Tyr Phe Thr Asn Asp Phe Ala Pro Tyr Leu Met
                245                 250                 255

Arg Phe Asp Asp Asn Asp Tyr Asn Ser Asn Arg Phe Ser Asp His Met
            260                 265                 270

Ser Glu Thr Gly Tyr Tyr Met Phe Val Val Lys Lys Ser Glu Val Lys
        275                 280                 285

Pro Phe Glu Ile Ile Phe Ala Lys Tyr Val Ser Asn Val Val Tyr Glu
    290                 295                 300

Tyr Thr Asn Asn Tyr Tyr Met Val Asp Asn Arg Val Phe Val Thr
305                 310                 315                 320

Phe Asp Lys Ile Arg Phe Met Ile Ser Tyr Asn Leu Val Lys Glu Thr
                325                 330                 335

Gly Ile Glu Ile Pro His Ser Gln Asp Val Cys Asn Asp Glu Thr Ala
            340                 345                 350

Ala Gln Asn Cys Lys Lys Cys His Phe Val Asp Val His His Thr Phe
        355                 360                 365

Lys Ala Ala Leu Thr Ser Tyr Phe Asn Leu Asp Met Tyr Tyr Ala Gln
    370                 375                 380

Thr Thr Phe Val Thr Leu Leu Gln Ser Leu Gly Glu Arg Lys Cys Gly
```

```
                385                 390                 395                 400
        Phe Leu Leu Ser Lys Leu Tyr Glu Met Tyr Gln Asp Lys Asn Leu Phe
                        405                 410                 415

Thr Leu Pro Ile Met Leu Ser Arg Lys Glu Ser Asn Glu Ile Glu Thr
                        420                 425                 430

Ala Ser Asn Asn Phe Phe Val Ser Pro Tyr Val Ser Gln Ile Leu Lys
                        435                 440                 445

Tyr Ser Glu Ser Val Gln Phe Pro Asp Asn Pro Asn Lys Tyr Val
                450                 455                 460

Val Asp Asn Leu Asn Leu Ile Val Asn Lys Lys Ser Thr Leu Thr Tyr
        465                 470                 475                 480

Lys Tyr Ser Ser Val Ala Asn Leu Leu Phe Asn Asn Tyr Lys Tyr His
                        485                 490                 495

Asp Asn Ile Ala Ser Asn Asn Ala Glu Asn Leu Lys Lys Val Lys
                        500                 505                 510

Lys Glu Asp Gly Ser Met His Ile Val Glu Gln Tyr Leu Thr Gln Asn
                        515                 520                 525

Val Asp Asn Val Lys Gly His Asn Phe Ile Val Leu Ser Phe Lys Asn
                530                 535                 540

Glu Glu Arg Leu Thr Ile Ala Lys Lys Asn Lys Glu Phe Tyr Trp Ile
        545                 550                 555                 560

Ser Gly Glu Ile Lys Asp Val Asp Val Ser Gln Val Ile Gln Lys Tyr
                        565                 570                 575

Asn Arg Phe Lys His His Met Phe Val Ile Gly Lys Val Asn Arg Arg
                        580                 585                 590

Glu Ser Thr Thr Leu His Asn Asn Leu Leu Lys Leu Ala Leu Ile
                        595                 600                 605

Leu Gln Gly Leu Val Pro Leu Ser Asp Ala Ile Thr Phe Ala Glu Gln
                        610                 615                 620

Lys Leu Asn Cys Lys Tyr Lys Lys Phe Glu Phe Asn
        625                 630                 635

<210> SEQ ID NO 8
<211> LENGTH: 222
<212> TYPE: PRT
<213> ORGANISM: Autographa californica nucleopolyhedrovirus

<400> SEQUENCE: 8

Met Thr Gln Ile Asn Phe Asn Ala Ser Tyr Thr Ser Ala Ser Thr Pro
1               5                   10                  15

Ser Arg Ala Ser Phe Asp Asn Ser Tyr Ser Glu Phe Cys Asp Lys Gln
                20                  25                  30

Pro Asn Asp Tyr Leu Ser Tyr Tyr Asn His Pro Thr Pro Asp Gly Ala
            35                  40                  45

Asp Thr Val Ile Ser Asp Ser Glu Thr Ala Ala Ser Asn Phe Leu
        50                  55                  60

Ala Ser Val Asn Ser Leu Thr Asp Asn Asp Leu Val Glu Cys Leu Leu
65                  70                  75                  80

Lys Thr Thr Asp Asn Leu Glu Glu Ala Val Ser Ser Ala Tyr Tyr Ser
                85                  90                  95

Glu Ser Leu Glu Gln Pro Val Val Glu Gln Pro Ser Pro Ser Ser Ala
                100                 105                 110

Tyr His Ala Glu Ser Phe Glu His Ser Ala Gly Val Asn Gln Pro Ser
            115                 120                 125
```

```
Ala Thr Gly Thr Lys Arg Lys Leu Asp Glu Tyr Leu Asp Asn Ser Gln
    130                 135                 140
Gly Val Val Gly Gln Phe Asn Lys Ile Lys Leu Arg Pro Lys Tyr Lys
145                 150                 155                 160
Lys Ser Thr Ile Gln Ser Cys Ala Thr Leu Glu Gln Thr Ile Asn His
                165                 170                 175
Asn Thr Asn Ile Cys Thr Val Ala Ser Thr Gln Glu Ile Thr His Tyr
            180                 185                 190
Phe Thr Asn Asp Phe Ala Pro Tyr Leu Met Arg Phe Asp Asp Asn Asp
        195                 200                 205
Tyr Asn Ser Asn Arg Phe Ser Asp His Met Ser Glu Thr Gly
210                 215                 220
```

<210> SEQ ID NO 9
<211> LENGTH: 276
<212> TYPE: PRT
<213> ORGANISM: Autographa californica nucleopolyhedrovirus

<400> SEQUENCE: 9

```
Met Ile Arg Thr Ser Ser His Val Leu Asn Val Gln Glu Asn Ile Met
1               5                   10                  15
Thr Ser Asn Cys Ala Ser Ser Pro Tyr Ser Cys Glu Ala Thr Ser Ala
                20                  25                  30
Cys Ala Glu Ala Gln Gln Leu Gln Val Asp Thr Gly Gly Asp Lys Ile
            35                  40                  45
Val Asn Asn Gln Val Thr Met Thr Gln Ile Asn Phe Asn Ala Ser Tyr
        50                  55                  60
Thr Ser Ala Ser Thr Pro Ser Arg Ala Ser Phe Asp Asn Ser Tyr Ser
65                  70                  75                  80
Glu Phe Cys Asp Lys Gln Pro Asn Asp Tyr Leu Ser Tyr Tyr Asn His
                85                  90                  95
Pro Thr Pro Asp Gly Ala Asp Thr Val Ile Ser Asp Ser Glu Thr Ala
                100                 105                 110
Ala Ala Ser Asn Phe Leu Ala Ser Val Asn Ser Leu Thr Asp Asn Asp
            115                 120                 125
Leu Val Glu Cys Leu Leu Lys Thr Thr Asp Asn Leu Glu Glu Ala Val
        130                 135                 140
Ser Ser Ala Tyr Tyr Ser Glu Ser Leu Glu Gln Pro Val Val Glu Gln
145                 150                 155                 160
Pro Ser Pro Ser Ser Ala Tyr His Ala Glu Ser Phe Glu His Ser Ala
                165                 170                 175
Gly Val Asn Gln Pro Ser Ala Thr Gly Thr Lys Arg Lys Leu Asp Glu
            180                 185                 190
Tyr Leu Asp Asn Ser Gln Gly Val Val Gly Gln Phe Asn Lys Ile Lys
        195                 200                 205
Leu Arg Pro Lys Tyr Lys Lys Ser Thr Ile Gln Ser Cys Ala Thr Leu
    210                 215                 220
Glu Gln Thr Ile Asn His Asn Thr Asn Ile Cys Thr Val Ala Ser Thr
225                 230                 235                 240
Gln Glu Ile Thr His Tyr Phe Thr Asn Asp Phe Ala Pro Tyr Leu Met
                245                 250                 255
Arg Phe Asp Asp Asn Asp Tyr Asn Ser Asn Arg Phe Ser Asp His Met
                260                 265                 270
Ser Glu Thr Gly
            275
```

<210> SEQ ID NO 10
<211> LENGTH: 128
<212> TYPE: DNA
<213> ORGANISM: Autographa californica nucleopolyhedrovirus

<400> SEQUENCE: 10

```
atcatggaga taattaaaat gataaccatc tcgcaaataa ataagtattt tactgttttc      60
gtaacagttt tgtaataaaa aaacctataa atattccgga ttattcatac cgtcccacca     120
tcgggcgc                                                              128
```

<210> SEQ ID NO 11
<211> LENGTH: 122
<212> TYPE: DNA
<213> ORGANISM: Autographa californica nucleopolyhedrovirus

<400> SEQUENCE: 11

```
atacggacct taattcaac ccaacacaat atattatagt taaataagaa ttattatcaa       60
atcatttgta tattaattaa aatactatac tgtaaattac attttattta caatcactcg     120
ac                                                                    122
```

<210> SEQ ID NO 12
<211> LENGTH: 571
<212> TYPE: DNA
<213> ORGANISM: Artificial Sequence
<220> FEATURE:
<223> OTHER INFORMATION: Description of Artificial Sequence: Synthetic
      recombinant chimeric promoter

<400> SEQUENCE: 12

```
aaaaacatcg attagggtga ctgaaggtta cattggggta ggttatggtt aatacgtaat      60
ggtttaacac caaaacgata tcatggattt tatataaggt gtaataatat ttttaatgag     120
tggacgcgtc gggtcaatgt cctgcctatt gacgtcataa catattaggt gattatatta    180
aaaatagttt aaactcaaat attacttgca agtttaagtt tcatcataat ctgatcataa    240
gtttcaccca acagaaacc aaaagcataa ctatcgaata tctttagctt cccatgaaga      300
aagattaccg taaccatcac taggatttta tacgattgta gaaaataaag tattctcagt    360
ctcttttcag agcgctataa aaaggggtgc attctcggta agagtacagt tgaactcaca    420
tcgagttaac tccacgctgc agtctcgaga tacggacctt taattcaacc caacacaata    480
tattatagtt aaataagaat tattatcaaa tcatttgtat attaattaaa atactatact    540
gtaaattaca ttttatttac aatcactcga c                                    571
```

<210> SEQ ID NO 13
<211> LENGTH: 465
<212> TYPE: DNA
<213> ORGANISM: Artificial Sequence
<220> FEATURE:
<223> OTHER INFORMATION: Description of Artificial Sequence: Synthetic
      recombinant chimeric promoter

<400> SEQUENCE: 13

```
ggtaccaaat tccgttttgc gacgatgcag agttttgaa caggctgctc aaacacatag       60
atccgtaccc gctcagtcgg atgtattaca atgcagccaa taccatgttt tacacgacta    120
tggaaaacta tgccgtgtcc aattgcaagt tcaacattga ggattacaat aacatattta    180
aggtgatgga aatattagg aaacacagca acaaaaattc aaacgaccaa gacgagttaa     240
```

```
acatatattt gggagttcag tcgtcgaatg caaagcgtaa aaaatattaa taaggtaaaa      300
attacagcta cataaattac acaatttaaa ctgcagtctg gagatacgga cctttaattc      360
aacccaacac aatatattat agttaaataa gaattattat caaatcattt gtatattaat      420
taaaatacta tactgtaaat tacattttat ttacaatcac tcgac                     465

<210> SEQ ID NO 14
<211> LENGTH: 436
<212> TYPE: DNA
<213> ORGANISM: Autographa californica nucleopolyhedrovirus

<400> SEQUENCE: 14
aaaaacatcg attagggtga ctgaaggtta cattggggta ggttatggtt aatacgtaat       60
ggtttaacac caaaacgata tcatggattt tatataaggt gtaataatat ttttaatgag      120
tggacgcgtc gggtcaatgt cctgcctatt gacgtcataa catattaggt gattatatta      180
aaaatagttt aaactcaaat attacttgca agtttaagtt tcatcataat ctgatcataa      240 gtttcacccca acagaaacc aaaagcataa ctatcgaata tctttagctt cccatgaaga      300
aagattaccg taaccatcac taggattttta tacgattgta gaaaataaag tattctcagt      360
ctcttttcag agcgctataa aaaggggtgc attctcggta agagtacagt tgaactcaca      420
tcgagttaac tccacg                                                     436

<210> SEQ ID NO 15
<211> LENGTH: 1176
<212> TYPE: DNA
<213> ORGANISM: Artificial Sequence
<220> FEATURE:
<223> OTHER INFORMATION: Description of Artificial Sequence: Synthetic
      recombinant chimeric promoter

<400> SEQUENCE: 15
cttgaatgtt agtgaaaccc cctgcgacac aagtattaca ttccttagtg cttgaatcct       60
ttaggaaaga aaagccaatt ttcaaaatct tagcacttgt taactcgcga aaaagaccaa      120
cagatttccc atactacaat tcgacattag aaatgtaaac ccattatcat tatttacgcc      180
tcatttccat ccaataataa gtttaagtac gttgagataa aactggctta cctagaactt      240
gacatggcga cctcttgcac tctgtatctc aagtcaactt tctctatcca aatatttgat      300
aacatttgac atgatattga agtaagattg ttactaaggc ttacattgta atattactga      360
cgcaagttct ttatcaataa aatagctgaa aacaaaaaaa aaaacatcga ttagggtgac      420
tgaaggttac attggggtag gttatggtta atacgtaatg gtttaacacc aaaacgatat      480
catggattga ctttataaat tttatataag gtgtaataat attttttaatg agtggacgcg      540 tcgggtcaat gtcctgccta ttgacgtcat aacatattag gtgattatat taaaaatact      600
caaatattac ttgcaagttt aagtttcatc ataatctgat cataagtttc acccaaacag      660
aaaccaaaag cataactatc tgctatttga atatctttag cttcccatga agaaagatta      720
ccgtaaccat cactaggatt ttatacgatt gtagaaaata agtattctc agtctctttt      780 cagtttaaaa tctgctggca ttttacaag tcgctgtatc agtcaatgtt tatacaatat      840
gtcaatgtac tttcgtatta atcagaaaaa aatattctac tagttttgat aagctatcac      900
ttttgttaca ttgtactgcc ctttacagtt catcaggtat ttatgaatga catattggag      960
aaacatcgta atcagtccag tataaaaagg ggtgcattct cggtaagagt acagttgaac     1020
tcacatcgag ttaactccac gctgcagtct cgagatacgg acctttaatt caacccaaca     1080
```

-continued

```
caatatatta tagttaaata agaattatta tcaaatcatt tgtatattaa ttaaaatact    1140
atactgtaaa ttacatttta tttacaatca ctcgac                              1176

<210> SEQ ID NO 16
<211> LENGTH: 250
<212> TYPE: DNA
<213> ORGANISM: Artificial Sequence
<220> FEATURE:
<223> OTHER INFORMATION: Description of Artificial Sequence: Synthetic
      recombinant chimeric promoter

<400> SEQUENCE: 16
atcatggaga taattaaaat gataaccatc tcgcaaataa ataagtattt tactgttttc      60
gtaacagttt tgtaataaaa aaacctataa atattccgga ttattcatac cgtcccacca    120
tcgggcgcat acggaccttt aattcaaccc aacacaatat attatagtta aataagaatt    180
attatcaaat catttgtata ttaattaaaa tactatactg taaattacat tttatttaca    240
atcactcgac                                                           250

<210> SEQ ID NO 17
<211> LENGTH: 3163
<212> TYPE: DNA
<213> ORGANISM: Artificial Sequence
<220> FEATURE:
<223> OTHER INFORMATION: Description of Artificial Sequence: Synthetic
      recombinant expression cassette

<400> SEQUENCE: 17
ttagttgaac tcgaacttct tgtacttgca gttgagcttt tgctcggcga atgtgatggc      60
gtcggagagt ggcaccagtc cctgcaggat caaggccaag agcttcagca agttgttgtg    120
cagtgtagtt gactcgcgac ggttgacctt gccgatcacg aacatgtggt gcttgaatct    180
gttgtacttt tggatgacct ggctcacatc aacgtccttg atttcgccag agatccagta    240
gaactccttg ttcttcttag cgatggtcag cctttcctcg ttcttgaagg acaacacgat    300
gaagttgtga cccttaacgt tatcgacgtt ttgagtcaag tactgctcaa cgatgtgcat    360
gcttccgtct tccttcttga ccttcttgag gttctcggcg ttgttgttag aagcgatgtt    420
gtcgtggtac ttgtagttgt tgaagagcag gttagcgacg gacgagtact tgtatgtcag    480
agtgctcttc ttgttcacga tgaggttcag gttatcaacg acgtacttgt tgggagggtt    540
gtccgggaat tggacggact ccgagtactt gaggatctgg gaaacgtatg gcgagacgaa    600
gaagttgtta gaggcggttt cgatctcgtt tgattccttg cggctcagca tgatgggcaa    660
agtgaagagg ttcttgtcct ggtacatctc gtacaacttc gacaagagga atccacactt    720
acgctcgccg agtgattgca gcaaggtcac gaaggttgtc tgagcgtagt acatatcgag    780
gttgaagtag gaggtcagag cggccttgaa tgtgtggtgg acgtccacga agtgacactt    840
cttgcagttt tgagcggcgg tctcatcgtt gcagacgtcc tgtgagtgtg ggatttcgat    900
gccagtctcc ttaaccaggt tgtagctgat catgaagcgg atcttatcga aggtcacaac    960
gaacacacgg ttgtcaacca tgtagtagtt gtttgtgtac tcgtagacca cgttagagac   1020
gtacttggcg aagatgattt cgaaaggctt cacctcggac ttcttaacga cgaacatgta   1080
gtaaccggtt tcagacatgt gatcggagaa tctgttcgag ttgtagtcgt tatcgtcgaa   1140
cctcatcagg tagggggcga agtcgtttgt gaagtagtga gtgatctcct gggtggaagc   1200
cactgtacag atgttagtgt tgtggttgat ggtttgttcc agtgtagcgc atgactggat   1260
ggtgctcttc ttgtacttag gtctcaactt gatcttgttg aattgaccca caactccctg   1320
```

-continued

```
ggagttatcc aggtactcgt ccaacttcct cttggtgcct gtggccgacg gctggttgac      1380
accagcagag tgttcgaagg actcggcgtg gtaagctgag ctaggagagg gttgttcgac      1440
cactggctgt tcgagtgact cgctgtagta ggcagaggac acagcttcct ccaggttgtc      1500
agtggtcttg agcagacact ccaccaaatc gttgtcagtg agcgagttaa ctgaggcgag      1560
gaagttgcta gcggcagcgg tttcagagtc ggagatgaca gtatcagctc cgtccggggt      1620
tgggtggttg tagtaagaca agtaatcgtt aggttgcttg tcgcagaact ccgagtatga      1680
gttgtcgaag ctagcacgag agggagtgct ggcagaggtg taggaagcgt tgaagttgat      1740
ttgagtcatg gtgacctggt tgttcacgat cttatcgcca cctgtgtcca cctgcagttg      1800
ctgggcctca gcgcaggctg aagtggcctc acaggagtag gggctggaag cacagttgga      1860
agtcatgatg ttttcttgga cgttcaggac gtggctggat gtacggatca tagatctatt      1920
gggtcatcta gattcgaaag cggccgcgac tagtgagctc gtcgacgtag gcctttgaat      1980
tccgcgcgct tcggacccgg atccgcgccc gatggtggga cggtatgaat aatccggaat      2040
atttataggt ttttttatta caaaactgtt acgaaaacag taaaatactt atttatttgc      2100
gagatggtta tcattttaat tatctccatg atctattaat attccggagt atacatcgat      2160
gttgacccca acaaaagatt tataattaat cataatcacg aacaacaaca agtcaatgaa      2220
acaaataaac aagttgtcga taaaacattc ataaatgaca cagcaacata caattcttgc      2280
ataataaaaa tttaaatgac atcatatttg agaataacaa atgacattat ccctcgattg      2340
tgttttacaa gtagaattct acccgtaaag cgagtttagt tttgaaaaac aaatgacatc      2400
atttgtataa tgacatcatc ccctgattgt gttttacaag tagaattcta tccgtaaagc      2460
gagttcagtt ttgaaaacaa atgagtcata cctaaacacg ttaataatct tctgatatca      2520
gcttatgact caagttatga gccgtgtgca aaacatgaga taagtttatg acatcatcca      2580
ctgatcgtgc gttacaagta gaattctact cgtaaagcca gttcggttat gagccgtgtg      2640
caaaacatga catcagctta tgactcatac ttgattgtgt tttacgcgta gaattctact      2700
cgtaaagcga gttcggttat gagccgtgtg caaaacatga catcagctta tgagtcataa      2760
ttaatcgtgc gttacaagta gaattctact cgtaaagcga gttgaaggat catatttagt      2820
tgcgtttatg agataagatt gaaagcacgt gtaaaatgtt tcccgcgcgt tggcacaact      2880
atttacaatg cggccaagtt ataaaagatt ctaatctgat atgttttaaa acacctttgc      2940
ggcccgagtt gtttgcgtac gtgactagcg aagaagatgt gtggaccgca gaacagatag      3000
taaaacaaaa ccctagtatt ggagcaataa tcgatgagct catacggacc tttaattcaa      3060
cccaacacaa tatattatag ttaaataaga attattatca aatcatttgt atattaatta      3120
aaatactata ctgtaaatta cattttattt acaatcactc gac                       3163
```

<210> SEQ ID NO 18
<211> LENGTH: 3656
<212> TYPE: DNA
<213> ORGANISM: Artificial Sequence
<220> FEATURE:
<223> OTHER INFORMATION: Description of Artificial Sequence: Synthetic recombinant expression cassette

<400> SEQUENCE: 18

```
ttagttgaac tcgaacttct tgtacttgca gttgagcttt tgctcggcga atgtgatggc        60
gtcggagagt ggcaccagtc cctgcaggat caaggccaag agcttcagca agttgttgtg       120
cagtgtagtt gactcgcgac ggttgacctt gccgatcacg aacatgtggt gcttgaatct       180
```

```
gttgtacttt tggatgacct ggctcacatc aacgtccttg atttcgccag agatccagta    240
gaactccttg ttcttcttag cgatggtcag cctttcctcg ttcttgaagg acaacacgat    300
gaagttgtga cccttaacgt tatcgacgtt ttgagtcaag tactgctcaa cgatgtgcat    360
gcttccgtct tccttcttga ccttcttgag gttctcggcg ttgttgttag aagcgatgtt    420
gtcgtggtac ttgtagttgt tgaagagcag gttagcgacg gacgagtact tgtatgtcag    480
agtgctcttc ttgttcacga tgaggttcag gttatcaacg acgtacttgt tgggagggtt    540
gtccgggaat tggacggact ccgagtactt gaggatctgg gaaacgtatg gcgagacgaa    600
gaagttgtta gaggcggttt cgatctcgtt tgattccttg cggctcagca tgatgggcaa    660
agtgaagagg ttcttgtcct ggtacatctc gtacaacttc gacaagagga atccacactt    720
acgctcgccg agtgattgca gcaaggtcac gaaggttgtc tgagcgtagt acatatcgag    780
gttgaagtag gaggtcagag cggccttgaa tgtgtggtgg acgtccacga agtgacactt    840
cttgcagttt tgagcggcgg tctcatcgtt gcagacgtcc tgtgagtgtg ggatttcgat    900
gccagtctcc ttaaccaggt tgtagctgat catgaagcgg atcttatcga aggtcacaac    960
gaacacacgg ttgtcaacca tgtagtagtt gtttgtgtac tcgtagacca cgttagagac   1020
gtacttggcg aagatgattt cgaaaggctt cacctcggac ttcttaacga cgaacatgta   1080
gtaaccggtt tcagacatgt gatcggagaa tctgttcgag ttgtagtcgt tatcgtcgaa   1140
cctcatcagg tagggggcga agtcgtttgt gaagtagtga gtgatctcct gggtggaagc   1200
cactgtacag atgttagtgt tgtggttgat ggtttgttcc agtgtagcgc atgactggat   1260
ggtgctcttc ttgtacttag gtctcaactt gatcttgttg aattgaccca caactccctg   1320
ggagttatcc aggtactcgt ccaacttcct cttggtgcct gtggccgacg gctggttgac   1380
accagcagag tgttcgaagg actcggcgtg gtaagctgag ctaggagagg ttgttcgac    1440 cactggctgt tcgagtgact cgctgtagta ggcagaggac acagcttcct ccaggttgtc   1500
agtggtcttg agcagacact ccaccaaatc gttgtcagtg agcgagttaa ctgaggcgag   1560
gaagttgcta gcggcagcgg tttcagagtc ggagatgaca gtatcagctc cgtccggggt   1620
tgggtggttg tagtaagaca agtaatcgtt aggttgcttg tcgcagaact ccgagtatga   1680
gttgtcgaag ctagcacgag agggagtgct ggcagaggtg taggaagcgt tgaagttgat   1740
ttgagtcatg gtgacctggt tgttcacgat cttatcgcca cctgtgtcca cctgcagttg   1800
ctgggcctca gcgcaggctg aagtggcctc acaggagtag gggctggaag cacagttgga   1860
agtcatgatg ttttcttgga cgttcaggac gtggctggat gtacggatca tagatctatt   1920
gggtcatcta gattcgaaag cggccgcgac tagtgagctc gtcgacgtag gcctttgaat   1980
tccgcgcgct tcggacccggg atccgcgccc gatggtggga cggtatgaat aatccggaat   2040
atttataggt ttttttatta caaaactgtt acgaaaacag taaaatactt atttatttgc   2100
gagatggtta tcattttaat tatctccatg atctattaat attccggagt atacatcgat   2160
gttgacccca acaaaagatt tataattaat cataatcacg aacaacaaca agtcaatgaa   2220
acaaataaac aagttgtcga taaaacattc ataaatgaca cagcaacata caattcttgc   2280
ataataaaaa tttaaatgac atcatatttg agaataacaa atgacattat ccctcgattg   2340
tgttttacaa gtagaattct acccgtaaag cgagtttagt tttgaaaaac aaatgacatc   2400
atttgtataa tgcatcatc ccctgattgt gttttacaag tagaattcta tccgtaaagc    2460
gagttcagtt ttgaaaacaa atgagtcata cctaaacacg ttaataatct tctgatatca   2520
```

```
gcttatgact caagttatga gccgtgtgca aaacatgaga taagtttatg acatcatcca    2580
ctgatcgtgc gttacaagta gaattctact cgtaaagcca gttcggttat gagccgtgtg    2640
caaaacatga catcagctta tgactcatac ttgattgtgt tttacgcgta gaattctact    2700
cgtaaagcga gttcggttat gagccgtgtg caaaacatga catcagctta tgagtcataa    2760
ttaatcgtgc gttacaagta gaattctact cgtaaagcga gttgaaggat catatttagt    2820
tgcgtttatg agataagatt gaaagcacgt gtaaaatgtt tcccgcgcgt tggcacaact    2880
atttacaatg cggccaagtt ataaaagatt ctaatctgat atgttttaaa acacctttgc    2940
ggcccgagtt gtttgcgtac gtgactagcg aagaagatgt gtggaccgca gaacagatag    3000
taaaacaaaa ccctagtatt ggagcaataa tcgatgagct cgtcgacgta ggcctttgaa    3060
ttccgcgcgc ttcggaccgg gatccaaaaa catcgattag ggtgactgaa ggttacattg    3120
gggtaggtta tggttaatac gtaatggttt aacaccaaaa cgatatcatg gattttatat    3180
aaggtgtaat aatattttta atgagtggac gcgtcgggtc aatgtcctgc ctattgacgt    3240
cataacatat taggtgatta tattaaaaat agtttaaact caaatattac ttgcaagttt    3300
aagtttcatc ataatctgat cataagtttc acccaaacag aaaccaaaag cataactatc    3360
gaatatcttt agcttcccat gaagaaagat taccgtaacc atcactagga ttttatacga    3420
ttgtagaaaa taaagtattc tcagtctctt ttcagagcgc tataaaaagg ggtgcattct    3480
cggtaagagt acagttgaac tcacatcgag ttaactccac gctgcagtct cgagatacgg    3540
acctttaatt caacccaaca caatatatta tagttaaata agaattatta tcaaatcatt    3600
tgtatattaa ttaaaatact atactgtaaa ttacatttta tttacaatca ctcgac        3656
```

<210> SEQ ID NO 19
<211> LENGTH: 3541
<212> TYPE: DNA
<213> ORGANISM: Artificial Sequence
<220> FEATURE:
<223> OTHER INFORMATION: Description of Artificial Sequence: Synthetic recombinant expression cassette

<400> SEQUENCE: 19

```
ttagttgaac tcgaacttct tgtacttgca gttgagcttt tgctcggcga atgtgatggc      60
gtcggagagt ggcaccagtc cctgcaggat caaggccaag agcttcagca agttgttgtg     120
cagtgtagtt gactcgcgac ggttgacctt gccgatcacg aacatgtggt gcttgaatct     180
gttgtacttt tggatgacct ggctcacatc aacgtccttg atttcgccag agatccagta     240
gaactccttg ttcttcttag cgatggtcag cctttcctcg ttcttgaagg acaacacgat     300
gaagttgtga cccttaacgt tatcgacgtt ttgagtcaag tactgctcaa cgatgtgcat     360
gcttccgtct tccttcttga ccttcttgag gttctcggcg ttgttgttag aagcgatgtt     420
gtcgtggtac ttgtagttgt tgaagagcag gttagcgacg gacgagtact tgtatgtcag     480
agtgctcttc ttgttcacga tgaggttcag gttatcaacg acgtacttgt tgggagggtt     540
gtccgggaat tggacggact ccgagtactt gaggatctgg gaaacgtatg gcgagacgaa     600
gaagttgtta gaggcggttt cgatctcgtt tgattccttg cggctcagca tgatgggcaa     660
agtgaagagg ttcttgtcct ggtacatctc gtacaacttc gacaagagga atccacactt     720
acgctcgccg agtgattgca gcaaggtcac gaaggttgtc tgagcgtagt acatatcgag     780
gttgaagtag gaggtcagag cggccttgaa tgtgtggtgg acgtccacga agtgacactt     840
cttgcagttt tgagcggcgg tctcatcgtt gcagacgtcc tgtgagtgtg ggatttcgat     900
```

```
gccagtctcc ttaaccaggt tgtagctgat catgaagcgg atcttatcga aggtcacaac    960
gaacacacgg ttgtcaacca tgtagtagtt gtttgtgtac tcgtagacca cgttagagac   1020
gtacttggcg aagatgattt cgaaaggctt cacctcggac ttcttaacga cgaacatgta   1080
gtaaccggtt tcagacatgt gatcggagaa tctgttcgag ttgtagtcgt tatcgtcgaa   1140
cctcatcagg taggggggcga agtcgtttgt gaagtagtga gtgatctcct gggtggaagc   1200
cactgtacag atgttagtgt tgtggttgat ggtttgttcc agtgtagcgc atgactggat   1260
ggtgctcttc ttgtacttag gtctcaactt gatcttgttg aattgaccca caactccctg   1320
ggagttatcc aggtactcgt ccaacttcct cttggtgcct gtggccgacg gctggttgac   1380
accagcagag tgttcgaagg actcggcgtg gtaagctgag ctaggagagg gttgttcgac   1440
cactggctgt tcgagtgact cgctgtagta ggcagaggac acagcttcct ccaggttgtc   1500
agtggtcttg agcagacact ccaccaaatc gttgtcagtg agcgagttaa ctgaggcgag   1560
gaagttgcta gcggcagcgg tttcagagtc ggagatgaca gtatcagctc cgtccggggt   1620
tgggtggttg tagtaagaca agtaatcgtt aggttgcttg tcgcagaact ccgagtatga   1680
gttgtcgaag ctagcacgag agggagtgct ggcagaggtg taggaagcgt tgaagttgat   1740
ttgagtcatg gtgacctggt tgttcacgat cttatcgcca cctgtgtcca cctgcagttg   1800
ctgggcctca gcgcaggctg aagtggcctc acaggagtag gggctggaag cacagttgga   1860
agtcatgatg ttttcttgga cgttcaggac gtggctggat gtacggatca tagatctatc   1920
tagattcgaa agcggccgcg actagtgagc tcgtcgacgt aggcctttga attccgcgcg   1980
cttcggaccg ggatccgcgc ccgatggtgg gacggtatga ataatccgga atatttatag   2040
gtttttttat tacaaaactg ttacgaaaac agtaaaatac ttatttattt gcgagatggt   2100
tatcatttta attatctcca tgatctatta atattccgga gtatacatcg atgttgaccc   2160
caacaaaaga tttataatta atcataatca cgaacaacaa caagtcaatg aaacaaataa   2220
acaagttgtc gataaaacat tcataaatga cacagcaaca tacaattctt gcataataaa   2280
aatttaaatg acatcatatt tgagaataac aaatgacatt atccctcgat tgtgttttac   2340
aagtagaatt ctacccgtaa agcgagttta gttttgaaaa acaaatgaca tcatttgtat   2400
aatgacatca tcccctgatt gtgttttaca agtagaattc tatccgtaaa gcgagttcag   2460
ttttgaaaac aaatgagtca tacctaaaca cgttaataat cttctgatat cagcttatga   2520
ctcaagttat gagccgtgtg caaaacatga gataagttta tgacatcatc cactgatcgt   2580
gcgttacaag tagaattcta ctcgtaaagc cagttcggtt atgagccgtg tgcaaaacat   2640
gacatcagct tatgactcat acttgattgt gttttacgcg tagaattcta ctcgtaaagc   2700
gagttcggtt atgagccgtg tgcaaaacat gacatcagct tatgagtcat aattaatcgt   2760
gcgttacaag tagaattcta ctcgtaaagc gagttgaagg atcatatta gttgcgttta   2820
tgagataaga ttgaaagcac gtgtaaaatg tttcccgcgc gttggcacaa ctatttacaa   2880
tgcggccaag ttataaaaga ttctaatctg atatgtttta aaacaccttt gcggcccgag   2940
ttgtttgcgt acgtgactag cgaagaagat gtgtggaccg cagaacagat agtaaaacaa   3000
aaccctagta ttggagcaat aatcgatgag ctcgtcgacg taggcctttg aattccgcgc   3060
gcttcggacc gggatcggta ccaaattccg ttttgcgacg atgcagagtt tttgaacagg   3120
ctgctcaaac acatagatcc gtacccgctc agtcggatgt attacaatgc agccaatacc   3180
atgttttaca cgactatgga aaactatgcc gtgtccaatt gcaagttcaa cattgaggat   3240
tacaataaca tatttaaggt gatggaaaat attaggaaac acagcaacaa aaattcaaac   3300
```

```
gaccaagacg agttaaacat atatttggga gttcagtcgt cgaatgcaaa gcgtaaaaaa    3360
tattaataag gtaaaaatta cagctacata aattacacaa tttaaactgc agtctggaga    3420
tacggacctt taattcaacc caacacaata tattatagtt aaataagaat tattatcaaa    3480
tcatttgtat attaattaaa atactatact gtaaattaca ttttatttac aatcactcga    3540
c                                                                    3541
```

<210> SEQ ID NO 20
<211> LENGTH: 3512
<212> TYPE: DNA
<213> ORGANISM: Artificial Sequence
<220> FEATURE:
<223> OTHER INFORMATION: Description of Artificial Sequence: Synthetic
      recombinant expression cassette

<400> SEQUENCE: 20

```
ttagttgaac tcgaacttct tgtacttgca gttgagcttt tgctcggcga atgtgatggc      60
gtcggagagt ggcaccagtc cctgcaggat caaggccaag agcttcagca agttgttgtg     120
cagtgtagtt gactcgcgac ggttgacctt gccgatcacg aacatgtggt gcttgaatct     180
gttgtacttt tggatgacct ggctcacatc aacgtccttg atttcgccag agatccagta     240
gaactccttg ttcttcttag cgatggtcag cctttcctcg ttcttgaagg acaacacgat     300
gaagttgtga cccttaacgt tatcgacgtt ttgagtcaag tactgctcaa cgatgtgcat     360
gcttccgtct tccttcttga ccttcttgag gttctcggcg ttgttgttag aagcgatgtt     420
gtcgtggtac ttgtagttgt tgaagagcag gttagcgacg gacgagtact tgtatgtcag     480
agtgctcttc ttgttcacga tgaggttcag gttatcaacg acgtacttgt tgggagggtt     540
gtccgggaat tggacggact ccgagtactt gaggatctgg gaaacgtatg gcagacgaa      600 gaagttgtta gaggcggttt cgatctcgtt tgattccttg cggctcagca tgatgggcaa     660
agtgaagagg ttcttgtcct ggtacatctc gtacaacttc gacaagagga atccacactt     720
acgctcgccg agtgattgca gcaaggtcac gaaggttgtc tgagcgtagt acatatcgag     780
gttgaagtag gaggtcagag cggccttgaa tgtgtggtgg acgtccacga agtgacactt     840
cttgcagttt tgagcggcgg tctcatcgtt gcagacgtcc tgtgagtgtg ggatttcgat     900
gccagtctcc ttaaccaggt tgtagctgat catgaagcgg atcttatcga aggtcacaac     960
gaacacacgg ttgtcaacca tgtagtagtt gtttgtgtac tcgtagacca cgttagagac    1020
gtacttggcg aagatgattt cgaaaggctt cacctcggac ttcttaacga cgaacatgta    1080
gtaaccggtt tcagacatgt gatcggagaa tctgttcgag ttgtagtcgt tatcgtcgaa    1140
cctcatcagg taggggggcga agtcgttgt gaagtagtga gtgatctcct gggtggaagc    1200
cactgtacag atgttagtgt tgtggttgat ggtttgttcc agtgtagcgc atgactggat    1260
ggtgctcttc ttgtacttag gtctcaactt gatcttgttg aattgaccca caactccctg    1320
ggagttatcc aggtactcgt ccaacttcct cttggtgcct gtggccgacg gctggttgac    1380
accagcagag tgttcgaagg actcggcgtg gtaagctgag ctaggagagg ttgttcgac     1440 cactggctgt tcgagtgact cgctgtagta ggcagaggac acagcttcct ccaggttgtc    1500
agtggtcttg agcagacact ccaccaaatc gttgtcagtg agcgagttaa ctgaggcgag    1560
gaagttgcta gcggcagcgg tttcagagtc ggagatgaca gtatcagctc cgtccggggt    1620
tgggtggttt tagtaagaca agtaatcgtt aggttgcttg tcgcagaact ccagagatga    1680
gttgtcgaag ctagcacgag agggagtgct ggcagaggtg taggaagcgt tgaagttgat    1740
```

```
ttgagtcatg gtgacctggt tgttcacgat cttatcgcca cctgtgtcca cctgcagttg   1800
ctgggcctca gcgcaggctg aagtggcctc acaggagtag gggctggaag cacagttgga   1860
agtcatgatg ttttcttgga cgttcaggac gtggctggat gtacggatca tagatctatc   1920
tagatgcatt cgcgaggtac cgagctcgaa ttcactggcc gtcgttttac aacgtcgtga   1980
ctgggaaaac cctggcgtta cccaacttaa tcgccttgca gcacatcccc ctttcgccag   2040
ctgctagcac catggctcga gcgtggagtt aactcgatgt gagttcaact gtactcttac   2100
cgagaatgca ccccttttta tagcgctctg aaaagagact gagaatactt tattttctac   2160
aatcgtataa atcctagtg atggttacgg taatctttct tcatgggaag ctaaagatat   2220
tcgatagtta tgcttttggt ttctgtttgg gtgaaactta tgatcagatt atgatgaaac   2280
ttaaacttgc aagtaatatt tgagtttaaa ctattttaa tataatcacc taatatgtta   2340
tgacgtcaat aggcaggaca ttgacccgac gcgtccactc attaaaaata ttattacacc   2400
ttatataaaa tccatgatat cgttttggtg ttaaaccatt acgtattaac cataacctac   2460
cccaatgtaa ccttcagtca ccctaatcga tgttttgta tacatcgatg ttgaccccaa   2520
caaaagattt ataattaatc ataatcacga acaacaacaa gtcaatgaaa caaataaaca   2580
agttgtcgat aaaacattca taaatgacac agcaacatac aattcttgca taataaaaat   2640
ttaaatgaca tcatatttga gaataacaaa tgacattatc cctcgattgt gttttacaag   2700
tagaattcta cccgtaaagc gagtttagtt ttgaaaaaca aatgacatca tttgtataat   2760
gacatcatcc cctgattgtg ttttacaagt agaattctat ccgtaaagcg agttcagttt   2820
tgaaaacaaa tgagtcatac ctaaacacgt taataatctt ctgatatcag cttatgactc   2880
aagttatgag ccgtgtgcaa acatgagat aagtttatga catcatccac tgatcgtgcg   2940
ttacaagtag aattctactc gtaaagccag ttcggttatg agccgtgtgc aaaacatgac   3000
atcagcttat gactcatact tgattgtgtt ttacgcgtag aattctactc gtaaagcgag   3060
ttcggttatg agccgtgtgc aaaacatgac atcagcttat gagtcataat taatcgtgcg   3120
ttacaagtag aattctactc gtaaagcgag ttgaaggatc atatttagtt gcgtttatga   3180
gataagattg aaagcacgtg taaatgtttt cccgcgcgtt ggcacaacta tttacaatgc   3240
ggccaagtta taaagattc taatctgata tgttttaaaa cacctttgcg gcccgagttg   3300
tttgcgtacg tgactagcga agaagatgtg tggaccgcag aacagatagt aaaacaaaac   3360
cctagtattg gagcaataat cgatgagctc atacggacct ttaattcaac ccaacacaat   3420
atattatagt taaataagaa ttattatcaa atcatttgta tattaattaa aatactatac   3480
tgtaaattac attttattta caatcactcg ac                                  3512
```

<210> SEQ ID NO 21  
<211> LENGTH: 4005  
<212> TYPE: DNA  
<213> ORGANISM: Artificial Sequence  
<220> FEATURE:  
<223> OTHER INFORMATION: Description of Artificial Sequence: Synthetic recombinant expression cassette

<400> SEQUENCE: 21

```
ttagttgaac tcgaacttct tgtacttgca gttgagcttt tgctcggcga atgtgatggc    60
gtcggagagt ggcaccagtc cctgcaggat caaggccaag agcttcagca agttgttgtg   120
cagtgtagtt gactcgcgac ggttgacctt gccgatcacg aacatgtggt gcttgaatct   180
gttgtacttt tggatgacct ggctcacatc aacgtccttg atttcgccag agatccagta   240
```

```
gaactccttg ttcttcttag cgatggtcag cctttcctcg ttcttgaagg acaacacgat    300
gaagttgtga cccttaacgt tatcgacgtt ttgagtcaag tactgctcaa cgatgtgcat    360
gcttccgtct tccttcttga ccttcttgag gttctcggcg ttgttgttag aagcgatgtt    420
gtcgtggtac ttgtagttgt tgaagagcag gttagcgacg gacgagtact tgtatgtcag    480
agtgctcttc ttgttcacga tgaggttcag gttatcaacg acgtacttgt tgggagggtt    540
gtccgggaat tggacggact ccgagtactt gaggatctgg gaaacgtatg gcgagacgaa    600
gaagttgtta gaggcggttt cgatctcgtt tgattccttg cggctcagca tgatgggcaa    660
agtgaagagg ttcttgtcct ggtacatctc gtacaacttc gacaagagga atccacactt    720
acgctcgccg agtgattgca gcaaggtcac gaaggttgtc tgagcgtagt acatatcgag    780
gttgaagtag gaggtcagag cggccttgaa tgtgtggtgg acgtccacga agtgacactt    840
cttgcagttt tgagcggcgg tctcatcgtt gcagacgtcc tgtgagtgtg ggatttcgat    900
gccagtctcc ttaaccaggt tgtagctgat catgaagcgg atcttatcga aggtcacaac    960
gaacacacgg ttgtcaacca tgtagtagtt gtttgtgtac tcgtagacca cgttagagac   1020
gtacttggcg aagatgattt cgaaaggctt cacctcggac ttcttaacga cgaacatgta   1080
gtaaccggtt tcagacatgt gatcggagaa tctgttcgag ttgtagtcgt tatcgtcgaa   1140
cctcatcagg taggggcgga agtcgtttgt gaagtagtga gtgatctcct gggtggaagc   1200
cactgtacag atgttagtgt tgtggttgat ggtttgttcc agtgtagcgc atgactggat   1260
ggtgctcttc ttgtacttag gtctcaactt gatcttgttg aattgaccca caactccctg   1320
ggagttatcc aggtactcgt ccaacttcct cttggtgcct gtggccgacg gctggttgac   1380
accagcagag tgttcgaagg actcggcgtg gtaagctgag ctaggagagg gttgttcgac   1440
cactggctgt tcgagtgact cgctgtagta ggcagaggac acagcttcct ccaggttgtc   1500
agtggtcttg agcagacact ccaccaaatc gttgtcagtg agcgagttaa ctgaggcgag   1560
gaagttgcta gcggcagcgg tttcagagtc ggagatgaca gtatcagctc cgtccggggt   1620
tgggtggttg tagtaagaca agtaatcgtt aggttgcttg tcgcagaact ccgagtatga   1680
gttgtcgaag ctagcacgag agggagtgct ggcagaggtg taggaagcgt tgaagttgat   1740
ttgagtcatg gtgacctggt tgttcacgat cttatcgcca cctgtgtcca cctgcagttg   1800
ctgggcctca gcgcaggctg aagtggcctc acaggagtag gggctggaag cacagttgga   1860
agtcatgatg ttttcttgga cgttcaggac gtggctggat gtacggatca tagatctatc   1920
tagatgcatt cgcgaggtac cgagctcgaa ttcactggcc gtcgttttac aacgtcgtga   1980
ctgggaaaac cctggcgtta cccaacttaa tcgccttgca gcacatcccc ctttcgccag   2040
ctgctagcac catggctcga gcgtggagtt aactcgatgt gagttcaact gtactcttac   2100
cgagaatgca cccctttta tagcgctctg aaaagagact gagaatactt tattttctac    2160
aatcgtataa aatcctagtg atggttacgg taatctttct tcatgggaag ctaaagatat   2220
tcgatagtta tgcttttggt ttctgttttgg gtgaaactta tgatcagatt atgatgaaac   2280
ttaaacttgc aagtaatatt tgagtttaaa ctattttaa tataatcacc taatatgtta    2340
tgacgtcaat aggcaggaca ttgacccgac gcgtccactc attaaaaata ttattacacc   2400
ttatataaaa tccatgatat cgttttggtg ttaaaccatt acgtattaac cataacctac   2460
cccaatgtaa ccttcagtca ccctaatcga tgttttgta tacatcgatg ttgaccccaa    2520
caaaagattt ataattaatc ataatcacga acaacaacaa gtcaatgaaa caaataaaca   2580
```

```
agttgtcgat aaaacattca taaatgacac agcaacatac aattcttgca taataaaaat    2640
ttaaatgaca tcatatttga gaataacaaa tgacattatc cctcgattgt gttttacaag    2700
tagaattcta cccgtaaagc gagtttagtt ttgaaaaaca aatgacatca tttgtataat    2760
gacatcatcc cctgattgtg ttttacaagt agaattctat ccgtaaagcg agttcagttt    2820
tgaaaacaaa tgagtcatac ctaaacacgt taataatctt ctgatatcag cttatgactc    2880
aagttatgag ccgtgtgcaa acatgagat aagtttatga catcatccac tgatcgtgcg    2940
ttacaagtag aattctactc gtaaagccag ttcggttatg agccgtgtgc aaaacatgac    3000
atcagcttat gactcatact tgattgtgtt ttacgcgtag aattctactc gtaaagcgag    3060
ttcggttatg agccgtgtgc aaaacatgac atcagcttat gagtcataat taatcgtgcg    3120
ttacaagtag aattctactc gtaaagcgag ttgaaggatc atatttagtt gcgtttatga    3180
gataagattg aaagcacgtg taaatgtttt cccgcgcgtt ggcacaacta tttacaatgc    3240
ggccaagtta taaagattc taatctgata tgttttaaaa caccttttgcg gcccgagttg    3300 tttgcgtacg tgactagcga agaagatgtg tggaccgcag aacagatagt aaaacaaaac    3360
cctagtattg gagcaataat cgatgagctc gtcgacgtag gcctttgaat tccgcgcgct    3420
tcggaccggg atccaaaaac atcgattagg gtgactgaag gttacattgg ggtaggttat    3480
ggttaatacg taatggttta acaccaaaac gatatcatgg atttatata aggtgtaata    3540 atatttttaa tgagtggacg cgtcgggtca atgtcctgcc tattgacgtc ataacatatt    3600
aggtgattat attaaaaata gtttaaactc aaatattact tgcaagttta agtttcatca    3660
taatctgatc ataagtttca cccaaacaga aaccaaaagc ataactatcg aatatcttta    3720
gcttcccatg aagaaagatt accgtaacca tcactaggat tttatacgat tgtagaaaat    3780
aaagtattct cagtctcttt tcagagcgct ataaaaaggg gtgcattctc ggtaagagta    3840
cagttgaact cacatcgagt taactccacg ctgcagtctc gagatacgga cctttaattc    3900
aacccaacac aatatattat agttaaataa gaattattat caaatcattt gtatattaat    3960
taaaatacta tactgtaaat tacattttat ttacaatcac tcgac                     4005
```

<210> SEQ ID NO 22
<211> LENGTH: 3898
<212> TYPE: DNA
<213> ORGANISM: Artificial Sequence
<220> FEATURE:
<223> OTHER INFORMATION: Description of Artificial Sequence: Synthetic recombinant expression cassette

<400> SEQUENCE: 22

```
ttagttgaac tcgaacttct tgtacttgca gttgagcttt tgctcggcga atgtgatggc      60
gtcggagagt ggcaccagtc cctgcaggat caaggccaag agcttcagca agttgttgtg     120
cagtgtagtt gactcgcgac ggttgacctt gccgatcacg aacatgtggt gcttgaatct     180
gttgtacttt tggatgacct ggctcacatc aacgtccttg atttcgccag agatccagta     240
gaactccttg ttcttcttag cgatggtcag cctttcctcg ttcttgaagg acaacacgat     300
gaagttgtga cccttaacgt tatcgacgtt ttgagtcaag tactgctcaa cgatgtgcat     360
gcttccgtct tccttcttga ccttcttgag gttctcggcg ttgttgttag aagcgatgtt     420
gtcgtggtac ttgtagttgt tgaagagcag gttagcgacg gacgagtact tgtatgtcag     480
agtgctcttc ttgttcacga tgaggttcag gttatcaacg acgtacttgt tgggagggtt     540
gtccgggaat tggacggact ccgagtactt gaggatctgg gaaacgtatg gcgagacgaa     600
```

```
gaagttgtta gaggcggttt cgatctcgtt tgattccttg cggctcagca tgatgggcaa    660
agtgaagagg ttcttgtcct ggtacatctc gtacaacttc gacaagagga atccacactt    720
acgctcgccg agtgattgca gcaaggtcac gaaggttgtc tgagcgtagt acatatcgag    780
gttgaagtag gaggtcagag cggccttgaa tgtgtggtgg acgtccacga agtgacactt    840
cttgcagttt tgagcggcgg tctcatcgtt gcagacgtcc tgtgagtgtg ggatttcgat    900
gccagtctcc ttaaccaggt tgtagctgat catgaagcgg atcttatcga aggtcacaac    960
gaacacacgg ttgtcaacca tgtagtagtt gtttgtgtac tcgtagacca cgttagagac   1020
gtacttggcg aagatgattt cgaaaggctt cacctcggac ttcttaacga cgaacatgta   1080
gtaaccggtt tcagacatgt gatcggagaa tctgttcgag ttgtagtcgt tatcgtcgaa   1140
cctcatcagg taggggcga agtcgtttgt gaagtagtga gtgatctcct gggtggaagc   1200
cactgtacag atgttagtgt tgtggttgat ggtttgttcc agtgtagcgc atgactggat   1260
ggtgctcttc ttgtacttag gtctcaactt gatcttgttg aattgaccca caactccctg   1320
ggagttatcc aggtactcgt ccaacttcct cttggtgcct gtggccgacg gctggttgac   1380
accagcagag tgttcgaagg actcggcgtg gtaagctgag ctaggagagg gttgttcgac   1440
cactggctgt tcgagtgact cgctgtagta ggcagaggac acagcttcct ccaggttgtc   1500
agtggtcttg agcagacact ccaccaaatc gttgtcagtg agcgagttaa ctgaggcgag   1560
gaagttgcta gcggcagcgg tttcagagtc ggagatgaca gtatcagctc cgtccggggt   1620
tgggtggttg tagtaagaca agtaatcgtt aggttgcttg tcgcagaact ccgagtatga   1680
gttgtcgaag ctagcacgag agggagtgct ggcagaggtg taggaagcgt tgaagttgat   1740
ttgagtcatg gtgacctggt tgttcacgat cttatcgcca cctgtgtcca cctgcagttg   1800
ctgggcctca gcgcaggctg aagtggcctc acaggagtag gggctggaag cacagttgga   1860
agtcatgatg ttttcttgga cgttcaggac gtggctggat gtacggatca tagatctatc   1920
tagatgcatt cgcgaggtac cgagctcgaa ttcactggcc gtcgttttac aacgtcgtga   1980
ctgggaaaac cctggcgtta cccaacttaa tcgccttgca gcacatcccc ctttcgccag   2040
ctgctagcac catggctcga gcgtggagtt aactcgatgt gagttcaact gtactcttac   2100
cgagaatgca cccctttta tagcgctctg aaaagagact gagaatactt tattttctac   2160
aatcgtataa atcctagtg atggttacgg taatctttct tcatgggaag ctaaagatat   2220
tcgatagtta tgcttttggt ttctgtttgg gtgaaactta tgatcagatt atgatgaaac   2280
ttaaacttgc aagtaatatt tgagtttaaa ctattttaa tataatcacc taatatgtta   2340
tgacgtcaat aggcaggaca ttgacccgac gcgtccactc attaaaaata ttattacacc   2400
ttatataaaa tccatgatat cgttttggtg ttaaaccatt acgtattaac cataacctac   2460
cccaatgtaa ccttcagtca ccctaatcga tgttttgta tacatcgatg ttgacccaa    2520 caaaagattt ataattaatc ataatcacga acaacaacaa gtcaatgaaa caaataaaca   2580
agttgtcgat aaaacattca taatgacac agcaacatac aattcttgca taataaaat    2640 ttaaatgaca tcatatttga gaataacaaa tgacattatc cctcgattgt gttttacaag   2700
tagaattcta cccgtaaagc gagtttagtt ttgaaaaaca aatgacatca tttgtataat   2760
gacatcatcc cctgattgtg ttttacaagt agaattctat ccgtaaagcg agttcagttt   2820
tgaaaacaaa tgagtcatac ctaaacacgt taataatctt ctgatatcag cttatgactc   2880
aagttatgag ccgtgtgcaa acatgagat aagtttatga catcatccac tgatcgtgcg   2940
ttacaagtag aattctactc gtaaagccag ttcggttatg agccgtgtgc aaaacatgac   3000
```

-continued

```
atcagcttat gactcatact tgattgtgtt ttacgcgtag aattctactc gtaaagcgag    3060
ttcggttatg agccgtgtgc aaaacatgac atcagcttat gagtcataat taatcgtgcg    3120
ttacaagtag aattctactc gtaaagcgag ttgaaggatc atatttagtt gcgtttatga    3180
gataagattg aaagcacgtg taaaatgttt cccgcgcgtt ggcacaacta tttacaatgc    3240
ggccaagtta taaagattc taatctgata tgttttaaaa cacctttgcg gcccgagttg     3300
tttgcgtacg tgactagcga agaagatgtg tggaccgcag aacagatagt aaaacaaaac    3360
cctagtattg gagcaataat cgatgagctc gtcgacgtag gcctttgaat tccgcgcgct    3420
tcggaccggg atcggtacca aattccgttt tgcgacgatg cagagttttt gaacaggctg    3480
ctcaaacaca tagatccgta cccgctcagt cggatgtatt acaatgcagc caataccatg    3540
ttttacacga ctatggaaaa ctatgccgtg tccaattgca agttcaacat tgaggattac    3600
aataacatat ttaaggtgat ggaaaatatt aggaaacaca gcaacaaaaa ttcaaacgac    3660
caagacgagt taaacatata tttgggagtt cagtcgtcga atgcaaagcg taaaaaatat    3720
taataaggta aaaattacag ctacataaat tacacaattt aaactgcagt ctggagatac    3780
ggacctttaa ttcaacccaa cacaatatat tatagttaaa taagaattat tatcaaatca    3840
tttgtatatt aattaaaata ctatactgta aattacattt tatttacaat cactcgac     3898
```

<210> SEQ ID NO 23
<211> LENGTH: 3179
<212> TYPE: DNA
<213> ORGANISM: Artificial Sequence
<220> FEATURE:
<223> OTHER INFORMATION: Description of Artificial Sequence: Synthetic
      recombinant expression cassette

<400> SEQUENCE: 23

```
ttagttgaac tcgaacttct tgtacttgca gttgagcttt tgctcggcga atgtgatggc      60
gtcggagagt ggcaccagtc cctgcaggat caaggccaag agcttcagca agttgttgtg     120
cagtgtagtt gactcgcgac ggttgacctt gccgatcacg aacatgtggt gcttgaatct     180
gttgtacttt tggatgacct ggctcacatc aacgtccttg atttcgccag agatccagta     240
gaactccttg ttcttcttag cgatggtcag cctttcctcg ttcttgaagg acaacacgat     300
gaagttgtga cccttaacgt tatcgacgtt ttgagtcaag tactgctcaa cgatgtgcat     360
gcttccgtct tccttcttga ccttcttgag gttctcggcg ttgttgttag aagcgatgtt     420
gtcgtggtac ttgtagttgt tgaagagcag gttagcgacg gacgagtact tgtatgtcag     480
agtgctcttc ttgttcacga tgaggttcag gttatcaacg acgtacttgt tgggagggtt     540
gtccgggaat tggacggact ccgagtactt gaggatctgg gaaacgtatg gcagagacgaa    600 gaagttgtta gaggcggttt cgatctcgtt tgattccttg cggctcagca tgatgggcaa    660
agtgaagagg ttcttgtcct ggtacatctc gtacaacttc gacaagagga atccacactt    720
acgctcgccg agtgattgca gcaaggtcac gaaggttgtc tgagcgtagt acatatcgag    780
gttgaagtag gaggtcagag cggccttgaa tgtgtggtgg acgtccacga agtgacactt    840
cttgcagttt tgagcggcgg tctcatcgtt gcagacgtcc tgtgagtgtg ggatttcgat    900
gccagtctcc ttaaccaggt tgtagctgat catgaagcgg atcttatcga aggtcacaac    960
gaacacacgg ttgtcaacca tgtagtagtt gtttgtgtac tcgtagacca cgttagagac   1020
gtacttggcg aagatgattt cgaaaggctt cacctcggac ttcttaacga cgaacatgta   1080
gtaaccggtt tcagacatgt gatcggagaa tctgttcgag ttgtagtcgt tatcgtcgaa   1140
```

```
cctcatcagg tagggggcga agtcgtttgt gaagtagtga gtgatctcct gggtggaagc    1200
cactgtacag atgttagtgt tgtggttgat ggtttgttcc agtgtagcgc atgactggat    1260
ggtgctcttc ttgtacttag gtctcaactt gatcttgttg aattgaccca caactccctg    1320
ggagttatcc aggtactcgt ccaacttcct cttggtgcct gtggccgacg gctggttgac    1380
accagcagag tgttcgaagg actcggcgtg gtaagctgag ctaggagagg gttgttcgac    1440
cactggctgt tcgagtgact cgctgtagta ggcagaggac acagcttcct ccaggttgtc    1500
agtggtcttg agcagacact ccaccaaatc gttgtcagtg agcgagttaa ctgaggcgag    1560
gaagttgcta gcggcagcgg tttcagagtc ggagatgaca gtatcagctc cgtccggggt    1620
tgggtggttg tagtaagaca agtaatcgtt aggttgcttg tcgcagaact ccgagtatga    1680
gttgtcgaag ctagcacgag agggagtgct ggcagaggtg taggaagcgt tgaagttgat    1740
ttgagtcatg gtgacctggt tgttcacgat cttatcgcca cctgtgtcca cctgcagttg    1800
ctgggcctca gcgcaggctg aagtggcctc acaggagtag gggctggaag cacagttgga    1860
agtcatgatg ttttcttgga cgttcaggac gtggctggat gtacggatca tagatctatt    1920
gggtcatcta gattcgaaag cggccgcgac tagtgagctc gtcgacgtag gcctttgaat    1980
tccgcgcgct tcggaccggg atccgcgccc gatggtggga cggtatgaat aatccggaat    2040
atttataggt tttttttatta caaaactgtt acgaaaacag taaaatactt atttatttgc    2100
gagatggtta tcattttaat tatctccatg atctattaat attccggagt atacatcgat    2160
gttgacccca acaaaagatt tataattaat cataatcacg aacaacaaca agtcaatgaa    2220
acaaataaac aagttgtcga taaaacattc ataaatgaca cagcaacata caattcttgc    2280
ataataaaaa tttaaatgac atcatatttg agaataacaa atgacattat ccctcgattg    2340
tgttttacaa gtagaattct acccgtaaag cgagtttagt tttgaaaaac aaatgacatc    2400
atttgtataa tgcatcatc ccctgattgt gttttacaag tagaattcta tccgtaaagc    2460
gagttcagtt ttgaaaacaa atgagtcata cctaaacacg ttaataatct tctgatatca    2520
gcttatgact caagttatga gccgtgtgca aacatgaga taagtttatg acatcatcca    2580
ctgatcgtgc gttacaagta gaattctact cgtaaagcca gttcggttat gagccgtgtg    2640
caaaacatga catcagctta tgactcatac ttgattgtgt tttacgcgta gaattctact    2700
cgtaaagcga gttcggttat gagccgtgtg caaaacatga catcagctta tgagtcataa    2760
ttaatcgtgc gttacaagta gaattctact cgtaaagcga gttgaaggat catatttagt    2820
tgcgtttatg agataagatt gaaagcacgt gtaaaatgtt tcccgcgcgt tggcacaact    2880
atttacaatg cggccaagtt ataaaagatt ctaatctgat atgttttaaa acacctttgc    2940
ggcccgagtt gtttgcgtac gtgactagcg aagaagatgt gtggaccgca gaacagatag    3000
taaaacaaaa ccctagtatt ggagcaataa tcgattccgg aatattaata gatcatggag    3060
ataattaaaa tgataaccat ctcgcaaata aataagtatt ttactgtttt cgtaacagtt    3120
ttgtaataaa aaaacctata aatattccgg attattcata ccgtcccacc atcgggcgc    3179
```

<210> SEQ ID NO 24
<211> LENGTH: 3528
<212> TYPE: DNA
<213> ORGANISM: Artificial Sequence
<220> FEATURE:
<223> OTHER INFORMATION: Description of Artificial Sequence: Synthetic recombinant expression cassette

<400> SEQUENCE: 24

```
ttagttgaac tcgaacttct tgtacttgca gttgagcttt tgctcggcga atgtgatggc      60
gtcggagagt ggcaccagtc cctgcaggat caaggccaag agcttcagca agttgttgtg     120
cagtgtagtt gactcgcgac ggttgacctt gccgatcacg aacatgtggt gcttgaatct     180
gttgtacttt tggatgacct ggctcacatc aacgtccttg atttcgccag agatccagta     240
gaactccttg ttcttcttag cgatggtcag cctttcctcg ttcttgaagg acaacacgat     300
gaagttgtga cccttaacgt tatcgacgtt ttgagtcaag tactgctcaa cgatgtgcat     360
gcttccgtct tccttcttga ccttcttgag gttctcggcg ttgttgttag aagcgatgtt     420
gtcgtggtac ttgtagttgt tgaagagcag gttagcgacg gacgagtact tgtatgtcag     480
agtgctcttc ttgttcacga tgaggttcag gttatcaacg acgtacttgt tgggagggtt     540
gtccgggaat tggacggact ccgagtactt gaggatctgg gaaacgtatg gcagacgaa      600 gaagttgtta gaggcggttt cgatctcgtt tgattccttg cggctcagca tgatgggcaa     660
agtgaagagg ttcttgtcct ggtacatctc gtacaacttc gacaagagga atccacactt     720
acgctcgccg agtgattgca gcaaggtcac gaaggttgtc tgagcgtagt acatatcgag     780
gttgaagtag gaggtcagag cggccttgaa tgtgtggtgg acgtccacga agtgacactt     840
cttgcagttt tgagcggcgg tctcatcgtt gcagacgtcc tgtgagtgtg ggatttcgat     900
gccagtctcc ttaaccaggt tgtagctgat catgaagcgg atcttatcga aggtcacaac     960
gaacacacgg ttgtcaacca tgtagtagtt gtttgtgtac tcgtagacca cgttagagac    1020
gtacttggcg aagatgattt cgaaaggctt cacctcggac ttcttaacga cgaacatgta    1080
gtaaccggtt tcagacatgt gatcggagaa tctgttcgag ttgtagtcgt tatcgtcgaa    1140
cctcatcagg taggggcga agtcgttgt gaagtagtga gtgatctcct gggtggaagc     1200
cactgtacag atgttagtgt tgtggttgat ggtttgttcc agtgtagcgc atgactggat    1260
ggtgctcttc ttgtacttag gtctcaactt gatcttgttg aattgaccca caactccctg    1320
ggagttatcc aggtactcgt ccaacttcct cttggtgcct gtggccgacg gctggttgac    1380
accagcagag tgttcgaagg actcggcgtg gtaagctgag ctaggagagg gttgttcgac    1440
cactggctgt tcgagtgact cgctgtagta ggcagaggac acagcttcct ccaggttgtc    1500
agtggtcttg agcagacact ccaccaaatc gttgtcagtg agcgagttaa ctgaggcgag    1560
gaagttgcta gcggcagcgg tttcagagtc ggagatgaca gtatcagctc cgtccggggt    1620
tgggtggttg tagtaagaca agtaatcgtt aggttgcttg tcgcagaact ccgagtatga    1680
gttgtcgaag ctagcacgag agggagtgct ggcagaggtg taggaagcgt tgaagttgat    1740
ttgagtcatg gtgacctggt tgttcacgat cttatcgcca cctgtgtcca cctgcagttg    1800
ctgggcctca gcgcaggctg aagtggcctc acaggagtag gggctggaag cacagttgga    1860
agtcatgatg tttcttgga cgttcaggac gtggctggat gtacggatca tagatctatc    1920
tagatgcatt cgcgaggtac cgagctcgaa ttcactggcc gtcgttttac aacgtcgtga    1980
ctgggaaaac cctggcgtta cccaacttaa tcgccttgca gcacatcccc ctttcgccag    2040
ctgctagcac catggctcga gcgtggagtt aactcgatgt gagttcaact gtactcttac    2100
cgagaatgca ccccttttta tagcgctctg aaaagagact gagaatactt tattttctac    2160
aatcgtataa aatcctagtg atggttacgg taatctttct tcatgggaag ctaaagatat    2220
tcgatagtta tgcttttggt ttctgtttgg gtgaaactta tgatcagatt atgatgaaac    2280
ttaaacttgc aagtaatatt tgagtttaaa ctattttaa tataatcacc taatatgtta    2340
```

```
tgacgtcaat aggcaggaca ttgacccgac gcgtccactc attaaaaata ttattacacc    2400
ttatataaaa tccatgatat cgttttggtg ttaaaccatt acgtattaac cataacctac    2460
cccaatgtaa ccttcagtca ccctaatcga tgttttttgta tacatcgatg ttgaccccaa   2520
caaaagattt ataattaatc ataatcacga acaacaacaa gtcaatgaaa caaataaaca    2580
agttgtcgat aaaacattca taaatgacac agcaacatac aattcttgca taataaaaat    2640
ttaaatgaca tcatatttga gaataacaaa tgacattatc cctcgattgt gttttacaag    2700
tagaattcta cccgtaaagc gagtttagtt ttgaaaaaca aatgacatca tttgtataat    2760
gacatcatcc cctgattgtg ttttacaagt agaattctat ccgtaaagcg agttcagttt    2820
tgaaaacaaa tgagtcatac ctaaacacgt taataatctt ctgatatcag cttatgactc    2880
aagttatgag ccgtgtgcaa acatgagat aagtttatga catcatccac tgatcgtgcg    2940
ttacaagtag aattctactc gtaaagccag ttcggttatg agccgtgtgc aaaacatgac    3000
atcagcttat gactcatact tgattgtgtt ttacgcgtag aattctactc gtaaagcgag    3060
ttcggttatg agccgtgtgc aaaacatgac atcagcttat gagtcataat taatcgtgcg    3120
ttacaagtag aattctactc gtaaagcgag ttgaaggatc atatttagtt gcgtttatga    3180
gataagattg aaagcacgtg taaatgtttt cccgcgcgtt ggcacaacta tttacaatgc    3240
ggccaagtta taaagattc taatctgata tgttttaaaa cacctttgcg gcccgagttg     3300
tttgcgtacg tgactagcga agaagatgtg tggaccgcag aacagatagt aaaacaaaac    3360
cctagtattg gagcaataat cgattccgga atattaatag atcatggaga taattaaaat    3420
gataaccatc tcgcaaataa ataagtattt tactgttttc gtaacagttt tgtaataaaa    3480
aaacctataa atattccgga ttattcatac cgtcccacca tcgggcgc                 3528
```

<210> SEQ ID NO 25
<211> LENGTH: 3291
<212> TYPE: DNA
<213> ORGANISM: Artificial Sequence
<220> FEATURE:
<223> OTHER INFORMATION: Description of Artificial Sequence: Synthetic
      recombinant expression cassette

<400> SEQUENCE: 25

```
ttagttgaac tcgaacttct tgtacttgca gttgagcttt tgctcggcga atgtgatggc      60
gtcggagagt ggcaccagtc cctgcaggat caaggccaag agcttcagca agttgttgtg     120
cagtgtagtt gactcgcgac ggttgacctt gccgatcacg aacatgtggt gcttgaatct     180
gttgtacttt tggatgacct ggctcacatc aacgtccttg atttcgccag agatccagta     240
gaactccttg ttcttcttag cgatggtcag ccttttcctcg ttcttgaagg acaacacgat    300
gaagttgtga cccttaacgt tatcgacgtt ttgagtcaag tactgctcaa cgatgtgcat    360
gcttccgtct tccttcttga ccttcttgag gttctcggcg ttgttgttag aagcgatgtt    420
gtcgtggtac ttgtagttgt tgaagagcag gttagcgacg acgagtact tgtatgtcag     480 agtgctcttc ttgttcacga tgaggttcag gttatcaacg acgtacttgt tgggagggtt    540
gtccgggaat tggacggact ccgagtactt gaggatctgg gaaacgtatg gcgagacgaa    600
gaagttgtta gaggcggttt cgatctcgtt tgattccttg cggctcagca tgatgggcaa    660
agtgaagagg ttcttgtcct ggtacatctc gtacaacttc gacaagagga atccacactt    720
acgctcgccg agtgattgca gcaaggtcac gaaggttgtc tgagcgtagt acatatcgag    780
gttgaagtag gaggtcagag cggccttgaa tgtgtggtgg acgtccacga agtgacactt    840
```

```
cttgcagttt tgagcggcgg tctcatcgtt gcagacgtcc tgtgagtgtg ggatttcgat    900
gccagtctcc ttaaccaggt tgtagctgat catgaagcgg atcttatcga aggtcacaac    960
gaacacacgg ttgtcaacca tgtagtagtt gtttgtgtac tcgtagacca cgttagagac   1020
gtacttggcg aagatgattt cgaaaggctt cacctcggac ttcttaacga cgaacatgta   1080
gtaaccggtt tcagacatgt gatcggagaa tctgttcgag ttgtagtcgt tatcgtcgaa   1140
cctcatcagg taggggcga agtcgtttgt gaagtagtga gtgatctcct gggtggaagc   1200
cactgtacag atgttagtgt tgtggttgat ggtttgttcc agtgtagcgc atgactggat   1260
ggtgctcttc ttgtacttag gtctcaactt gatcttgttg aattgaccca caactccctg   1320
ggagttatcc aggtactcgt ccaacttcct cttggtgcct gtggccgacg gctggttgac   1380
accagcagag tgttcgaagg actcggcgtg gtaagctgag ctaggagagg gttgttcgac   1440
cactggctgt tcgagtgact cgctgtagta ggcagaggac acagcttcct ccaggttgtc   1500
agtggtcttg agcagacact ccaccaaatc gttgtcagtg agcgagttaa ctgaggcgag   1560
gaagttgcta gcggcagcgg tttcagagtc ggagatgaca gtatcagctc cgtccggggt   1620
tgggtggttg tagtaagaca agtaatcgtt aggttgcttg tcgcagaact ccgagtatga   1680
gttgtcgaag ctagcacgag agggagtgct ggcagaggtg taggaagcgt tgaagttgat   1740
ttgagtcatg gtgacctggt tgttcacgat cttatcgcca cctgtgtcca cctgcagttg   1800
ctgggcctca gcgcaggctg aagtggcctc acaggagtag gggctggaag cacagttgga   1860
agtcatgatg ttttcttgga cgttcaggac gtggctggat gtacggatca tagatctatt   1920
gggtcatcta gattcgaaag cggccgcgac tagtgagctc gtcgacgtag gcctttgaat   1980
tccgcgcgct tcggaccggg atccgcgccc gatggtggga cggtatgaat aatccggaat   2040
atttataggt tttttttatta caaaactgtt acgaaaacag taaatactt atttatttgc   2100 gagatggtta tcattttaat tatctccatg atctattaat attccggagt atacatcgat   2160
gttgacccca acaaaagatt tataattaat cataatcacg aacaacaaca agtcaatgaa   2220
acaaataaac aagttgtcga taaaacattc ataaatgaca cagcaacata caattcttgc   2280
ataataaaaa tttaaatgac atcatatttg agaataacaa atgacattat ccctcgattg   2340
tgttttacaa gtagaattct acccgtaaag cgagtttagt tttgaaaaac aaatgacatc   2400
atttgtataa tgacatcatc ccctgattgt gttttacaag tagaattcta tccgtaaagc   2460
gagttcagtt ttgaaaacaa atgagtcata cctaaacacg ttaataatct tctgatatca   2520
gcttatgact caagttatga gccgtgtgca aaacatgaga taagtttatg acatcatcca   2580
ctgatcgtgc gttacaagta gaattctact cgtaaagcca gttcggttat gagccgtgtg   2640
caaaacatga catcagctta tgactcatac ttgattgtgt tttacgcgta gaattctact   2700
cgtaaagcga gttcggttat gagccgtgtg caaaacatga catcagctta tgagtcataa   2760
ttaatcgtgc gttacaagta gaattctact cgtaaagcga gttgaaggat catatttagt   2820
tgcgtttatg agataagatt gaaagcacgt gtaaaatgtt tcccgcgcgt tggcacaact   2880
atttacaatg cggccaagtt ataaaagatt ctaatctgat atgttttaaa acacctttgc   2940
ggcccgagtt gtttgcgtac gtgactagcg aagaagatgt gtggaccgca gaacagatag   3000
taaaacaaaa ccctagtatt ggagcaataa tcgatgagct catcatggag ataattaaaa   3060
tgataaccat ctcgcaaata aataagtatt ttactgtttt cgtaacagtt ttgtaataaa   3120
aaaacctata aatattccgg attattcata ccgtcccacc atcgggcgca tacgacctt   3180 taattcaacc caacacaata tattatagtt aaataagaat tattatcaaa tcatttgtat   3240
```

```
                     attaattaaa atactatact gtaaattaca ttttatttac aatcactcga c       3291

<210> SEQ ID NO 26
<211> LENGTH: 3640
<212> TYPE: DNA
<213> ORGANISM: Artificial Sequence
<220> FEATURE:
<223> OTHER INFORMATION: Description of Artificial Sequence: Synthetic
      recombinant expression cassette

<400> SEQUENCE: 26
ttagttgaac tcgaacttct tgtacttgca gttgagcttt tgctcggcga atgtgatggc          60
gtcggagagt ggcaccagtc cctgcaggat caaggccaag agcttcagca gttgttgtg         120 cagtgtagtt gactcgcgac ggttgacctt gccgatcacg aacatgtggt gcttgaatct        180
gttgtacttt tggatgacct ggctcacatc aacgtccttg atttcgccag agatccagta        240
gaactccttg ttcttcttag cgatggtcag ccttcctcg ttcttgaagg acaaacgat         300 gaagttgtga cccttaacgt tatcgacgtt ttgagtcaag tactgctcaa cgatgtgcat        360
gcttccgtct tccttcttga ccttcttgag gttctcggcg ttgttgttag aagcgatgtt        420
gtcgtggtac ttgtagttgt tgaagagcag gttagcgacg gacgagtact tgtatgtcag       480
agtgctcttc ttgttcacga tgaggttcag gttatcaacg acgtacttgt tgggagggtt       540
gtccgggaat tggacggact ccgagtactt tgaggatctgg gaaacgtatg gcgagacgaa     600
gaagttgtta gaggcggttt cgatctcgtt tgattccttg cggctcagca tgatgggcaa      660
agtgaagagg ttcttgtcct ggtacatctc gtacaacttc gacaagagga atccacactt     720
acgctcgccg agtgattgca gcaaggtcac gaaggttgtc tgagcgtagt acatatcgag    780
gttgaagtag gaggtcagag cggccttgaa tgtgtggtgg acgtccacga agtgacactt    840
cttgcagttt tgagcggcgg tctcatcgtt gcagacgtcc tgtgagtgtg ggatttcgat    900
gccagtctcc ttaaccaggt tgtagctgat catgaagcgg atcttatcga aggtcacaac    960
gaacacacgg ttgtcaacca tgtagtagtt gtttgtgtac tcgtagacca cgttagagac   1020
gtacttggcg aagatgattt cgaaaggctt cacctcggac ttcttaacga cgaacatgta   1080
gtaaccggtt tcagacatgt gatcggagaa tctgttcgag ttgtagtcgt tatcgtcgaa    1140
cctcatcagg taggggcgaa agtcgtttgt gaagtagtga gtgatctcct gggtggaagc   1200
cactgtacag atgttagtgt tgtggttgat ggtttgttcc agtgtagcgc atgactggat    1260
ggtgctcttc ttgtacttag gtctcaactt gatcttgttg aattgaccca caactccctg    1320
ggagttatcc aggtactcgt ccaacttcct cttggtgcct gtggccgacg ctggttgac     1380 accagcagag tgttcgaagg actcggcgtg gtaagctgag ctaggagagg gttgttcgac    1440
cactggctgt tcgagtgact cgctgtagta ggcagaggac acagcttcct ccaggttgtc   1500
agtggtcttg agcagacact ccaccaaatc gttgtcagtg agcgagttaa ctgaggcgag    1560
gaagttgcta gcggcagcgg tttcagagtc ggagatgaca gtatcagctc cgtccgggt    1620 tgggtggttg tagtaagaca agtaatcgtt aggttgcttg tcgcagaact ccgagtatga    1680
gttgtcgaag ctagcacgag agggagtgct ggcagaggtg taggaagcgt tgaagttgat    1740
ttgagtcatg gtgacctggt tgttcacgat cttatcgcca cctgtgtcca cctgcagttg    1800
ctgggcctca gcgcaggctg aagtggcctc acaggagtag gggctggaag cacagttgga    1860
agtcatgatg ttttcttgga cgttcaggac gtggctggat gtacggatca tagatctatc    1920
tagatgcatt cgcgaggtac cgagctcgaa ttcactggcc gtcgttttac aacgtcgtga    1980
```

```
ctgggaaaac cctggcgtta cccaacttaa tcgccttgca gcacatcccc ctttcgccag    2040
ctgctagcac catggctcga gcgtggagtt aactcgatgt gagttcaact gtactcttac    2100
cgagaatgca ccccttttta tagcgctctg aaaagagact gagaatactt tattttctac    2160
aatcgtataa aatcctagtg atggttacgg taatctttct tcatgggaag ctaaagatat    2220
tcgatagtta tgcttttggt ttctgtttgg gtgaaactta tgatcagatt atgatgaaac    2280
ttaaacttgc aagtaatatt tgagtttaaa ctattttaa tataatcacc taatatgtta    2340
tgacgtcaat aggcaggaca ttgacccgac gcgtccactc attaaaaata ttattacacc    2400
ttatataaaa tccatgatat cgttttggtg ttaaaccatt acgtattaac cataacctac    2460
cccaatgtaa ccttcagtca ccctaatcga tgttttgta tacatcgatg ttgaccccaa    2520
caaaagattt ataattaatc ataatcacga acaacaacaa gtcaatgaaa caaataaaca    2580
agttgtcgat aaaacattca taaatgacac agcaacatac aattcttgca taataaaaat    2640
ttaaatgaca tcatatttga gaataacaaa tgacattatc cctcgattgt gttttacaag    2700
tagaattcta cccgtaaagc gagtttagtt ttgaaaaaca aatgacatca tttgtataat    2760
gacatcatcc cctgattgtg ttttacaagt agaattctat ccgtaaagcg agttcagttt    2820
tgaaaacaaa tgagtcatac ctaaacacgt taataatctt ctgatatcag cttatgactc    2880
aagttatgag ccgtgtgcaa acatgagat aagtttatga catcatccac tgatcgtgcg    2940
ttacaagtag aattctactc gtaaagccag ttcggttatg agccgtgtgc aaaacatgac    3000
atcagcttat gactcatact tgattgtgtt tacgcgtag aattctactc gtaaagcgag    3060
ttcggttatg agccgtgtgc aaaacatgac atcagcttat gagtcataat taatcgtgcg    3120
ttacaagtag aattctactc gtaaagcgag ttgaaggatc atatttagtt gcgtttatga    3180
gataagattg aaagcacgtg taaatgtttt cccgcgcgtt ggcacaacta tttacaatgc    3240
ggccaagtta taaagattc taatctgata tgttttaaaa cacctttgcg gcccgagttg    3300
tttgcgtacg tgactagcga agaagatgtg tggaccgcag aacagatagt aaaacaaaac    3360
cctagtattg gagcaataat cgatgagctc atcatggaga taattaaaat gataaccatc    3420
tcgcaaataa ataagtattt tactgttttc gtaacagttt tgtaataaaa aaacctataa    3480
atattccgga ttattcatac cgtcccacca tcgggcgcat acggaccttt aattcaaccc    3540
aacacaatat attatagtta aataagaatt attatcaaat catttgtata ttaattaaaa    3600
tactatactg taaattacat tttatttaca atcactcgac                         3640
```

<210> SEQ ID NO 27
<211> LENGTH: 881
<212> TYPE: DNA
<213> ORGANISM: Autographa californica nucleopolyhedrovirus

<400> SEQUENCE: 27

```
atcgatgttg accccaacaa aagatttata attaatcata atcacgaaca acaacaagtc     60
aatgaaacaa ataaacaagt tgtcgataaa acattcataa atgacacagc aacatacaat    120
tcttgcataa taaaaattta atgacatca tatttgagaa taacaaatga cattatccct    180
cgattgtgtt ttacaagtag aattctaccc gtaaagcgag tttagttttg aaaacaaat    240 gacatcattt gtataatgac atcatcccct gattgtgttt tacaagtaga attctatccg    300
taaagcgagt tcagttttga aaacaaatga gtcataccta aacacgttaa taatcttctg    360
atatcagctt atgactcaag ttatgagccg tgtgcaaaac atgagataag tttatgacat    420
```

| | |
|---|---|
| catccactga tcgtgcgtta caagtagaat tctactcgta aagccagttc ggttatgagc | 480 |
| cgtgtgcaaa acatgacatc agcttatgac tcatacttga ttgtgtttta cgcgtagaat | 540 |
| tctactcgta aagcgagttc ggttatgagc cgtgtgcaaa acatgacatc agcttatgag | 600 |
| tcataattaa tcgtgcgtta caagtagaat tctactcgta aagcgagttg aaggatcata | 660 |
| tttagttgcg tttatgagat aagattgaaa gcacgtgtaa aatgtttccc gcgcgttggc | 720 |
| acaactattt acaatgcggc caagttataa aagattctaa tctgatatgt tttaaaacac | 780 |
| cttttgcggcc cgagttgttt gcgtacgtga ctagcgaaga agatgtgtgg accgcagaac | 840 |
| agatagtaaa acaaaaccct agtattggag caataatcga t | 881 |

<210> SEQ ID NO 28
<211> LENGTH: 2124
<212> TYPE: DNA
<213> ORGANISM: Artificial Sequence
<220> FEATURE:
<223> OTHER INFORMATION: Description of Artificial Sequence: Synthetic
recombinant DNA construct fusing the Ac-ie-01 cDNA to the polh
promoter

<400> SEQUENCE: 28

| | |
|---|---|
| atcatggaga taattaaaat gataaccatc tcgcaaataa ataagtattt tactgttttc | 60 |
| gtaacagttt tgtaataaaa aaacctataa atattccgga ttattcatac cgtcccacca | 120 |
| tcgggcgcgg atcccggtcc gaagcgcgcg gaattcaaag gcctacgtcg acgagctcac | 180 |
| tagtcgcggc cgcttttcgaa tctagataga tctatgatcc gtacatccag ccacgtcctg | 240 |
| aacgtccaag aaaacatcat gacttccaac tgtgcttcca gccccctactc ctgtgaggcc | 300 |
| acttcagcct gcgctgaggc ccagcaactg caggtggaca caggtggcga taagatcgtg | 360 |
| aacaaccagg tcaccatgac tcaaatcaac ttcaacgctt cctacacctc tgccagcact | 420 |
| ccctctcgtg ctagcttcga caactcatac tcggagttct gcgacaagca acctaacgat | 480 |
| tacttgtctt actacaacca cccaaccccg gacggagctg atactgtcat ctccgactct | 540 |
| gaaaccgctg ccgctagcaa cttcctcgcc tcagttaact cgctcactga caacgatttg | 600 |
| gtggagtgtc tgctcaagac cactgacaac ctggaggaag ctgtgtcctc tgcctactac | 660 |
| agcgagtcac tcgaacagcc agtggtcgaa caaccctctc ctagctcagc ttaccacgcc | 720 |
| gagtccttcg aacactctgc tggtgtcaac cagccgtcgg ccacaggcac caagaggaag | 780 |
| ttggacgagt acctggataa ctcccaggga gttgtgggtc aattcaacaa gatcaagttg | 840 |
| agacctaagt acaagaagag caccatccag tcatgcgcta cactggaaca aaccatcaac | 900 |
| cacaacacta acatctgtac agtggcttcc acccaggaga tcactcacta cttcacaaac | 960 |
| gacttcgccc cctacctgat gaggttcgac gataacgact acaactcgaa cagattctcc | 1020 |
| gatcacatgt ctgaaaccgg ttactacatg ttcgtcgtta agaagtccga ggtgaagcct | 1080 |
| ttcgaaatca tcttcgccaa gtacgtctct aacgtggtct acgagtacac aaacaactac | 1140 |
| tacatggttg acaaccgtgt gttcgttgtg accttcgata agatccgctt catgatcagc | 1200 |
| tacaacctgg ttaaggagac tggcatcgaa atcccacact cacaggacgt ctgcaacgat | 1260 |
| gagaccgccg ctcaaaactg caagaagtgt cacttcgtgg acgtccacca cacattcaag | 1320 |
| gccgctctga cctcctactt caacctcgat atgtactacg ctcagacaac cttcgtgacc | 1380 |
| ttgctgcaat cactcggcga gcgtaagtgt ggattcctct tgtcgaagtt gtacgagatg | 1440 |
| taccaggaca agaacctctt cactttgccc atcatgctga gccgcaagga atcaaacgag | 1500 |
| atcgaaaccg cctctaacaa cttcttcgtc tcgccatacg tttcccagat cctcaagtac | 1560 |

```
tcggagtccg tccaattccc ggacaaccct cccaacaagt acgtcgttga taacctgaac      1620
ctcatcgtga acaagaagag cactctgaca tacaagtact cgtccgtcgc taacctgctc      1680
ttcaacaact acaagtacca cgacaacatc gcttctaaca acaacgccga gaacctcaag      1740
aaggtcaaga aggaagacgg aagcatgcac atcgttgagc agtacttgac tcaaaacgtc      1800
gataacgtta agggtcacaa cttcatcgtg ttgtccttca agaacgagga aaggctgacc      1860
atcgctaaga agaacaagga gttctactgg atctctggcg aaatcaagga cgttgatgtg      1920
agccaggtca tccaaaagta caacagattc aagcaccaca tgttcgtgat cggcaaggtc      1980
aaccgtcgcg agtcaactac actgcacaac aacttgctga agctcttggc cttgatcctg      2040
cagggactgg tgccactctc cgacgccatc acattcgccg agcaaaagct caactgcaag      2100
tacaagaagt tcgagttcaa ctaa                                             2124

<210> SEQ ID NO 29
<211> LENGTH: 911
<212> TYPE: DNA
<213> ORGANISM: Artificial Sequence
<220> FEATURE:
<223> OTHER INFORMATION: Description of Artificial Sequence: Synthetic
      recombinant DNA construct fusing the GFP cDNA to the polh
      promoter

<400> SEQUENCE: 29
atcatggaga taattaaaat gataaccatc tcgcaaataa ataagtattt tactgttttc        60
gtaacagttt tgtaataaaa aaacctataa atattccgga ttattcatac cgtcccacca       120
tcgggcgcgg atccaaggcc actagtgcgg ccgctctgca gtctcgagca tgcggtacca       180
agcttgaatt catggtgagc aagggcgagg agctgttcac cggggtggtg cccatcctgg       240
tcgagctgga cggcgacgta aacggccaca gttcagcgt gtccggcgag ggcgagggcg        300
atgccaccta cggcaagctg accctgaagt tcatctgcac caccggcaag ctgcccgtgc       360
cctggcccac cctcgtgacc accctgacct acggcgtgca gtgcttcagc cgctaccccg       420
accacatgaa gcagcacgac ttcttcaagt ccgccatgcc cgaaggctac gtccaggagc       480
gcaccatctt cttcaaggac gacggcaact acaagacccg cgccgaggtg aagttcgagg       540
gcgacaccct ggtgaaccgc atcgagctga agggcatcga cttcaaggag gacggcaaca       600
tcctggggca caagctggag tacaactaca acagccacaa cgtctatatc atggccgaca       660
agcagaagaa cggcatcatg gtgaacttca gatccgcca caacatcgag gacggcagcg       720
tgcagctcgc cgaccactac cagcagaaca cccccatcgg cgacggcccc gtgctgctgc      780
ccgacaacca ctacctgagc acccagtccg ccctgagcaa agaccccaac gagaagcgcg      840
atcacatggt cctgctggag ttcgtgaccg ccgccgggat cactctcggc atggacgagc      900
tgtacaagta a                                                           911
```

BACULOVIRAL DNA ELEMENTS FOR THE EXPRESSION OF RECOMBINANT PROTEINS IN A HOST INSECT

RELATED APPLICATIONS

This application is a 35 U.S.C. §371 national stage filing of International Application No. PCT/EP2012/061088, filed on Jun. 12, 2012, the entire contents of which are explicitly incorporated herein by reference.

SEQUENCE LISTING

The instant application contains a Sequence Listing which has been submitted electronically in ASCII format and is hereby incorporated by reference in its entirety. Said ASCII copy, created on Jan. 5, 2017, is named 117814_27201 SL.txt and is 81,807 bytes in size.

FIELD OF THE INVENTION

The present invention may be included in the field of biotechnology and it covers nucleic acid sequences comprising, for example, promoters, homologous regions (hr) as enhancers, and sequences encoding transcriptional regulators, for example, the baculovirus Ac-ie-01 cDNA, or any combination thereof, which are able to increase the efficiency of recombinant protein expression, for example in insect larvae. Moreover, the present invention is also directed to the vectors themselves comprising the above mentioned nucleic acid sequences of the invention, insects infected, transformed, transduced or transfected with those sequences or vectors, and methods for producing proteins by using the aforesaid sequences, vectors or insects.

STATE OF THE ART

The baculovirus expression vector system (BEVS) is a well-established method for the production of recombinant proteins to be used as vaccines, therapeutic molecules or diagnostic reagents. With its potential for over-expression and rapid speed of development, BEVS is one of the most attractive choices for producing recombinant proteins for any purpose. The most employed baculovirus vector used in industry for recombinant protein expression is based on *Autographa californica* multinuclear polyhedrosis virus (AcMNPV) with *Spodoptera frugiperda* 9 (Sf9) or 21 (Sf21) insect cells as suitable expression hosts (1), as well as *Trichoplusia* of (*T. ni*) insect larvae as living biofactories (2). Since the BEVS was developed in the 80's (3), hundreds of recombinant proteins, ranging from cytosolic enzymes to membrane-bound proteins, have been successfully produced in baculovirus-infected insect cells.

Worldwide, about 70,000 tons of silk are produced annually in a process that converts a low-value substrate, the leaves of the mulberry tree, to a high-value protein-based product: silk. Insects are highly efficacious protein producers because of their accelerated metabolism. Lepidoptera such as *Bombyx mori* or *Trichoplusia ni*, are two of the most used insects in biotechnology. They grow in size about 5000 times in less than 2 weeks and produce more than a kilometer of silk per insect. While a cell from a silk gland may produce about 80 µg protein/cell/day, the best mammalian cell culture systems produces only about 50 pg protein/cell/day. Concerns arising from potential contamination by adventitious agents (such as viruses or prions) of recombinant proteins obtained from cultured mammalian cells are substantially lower, if not totally absent, in the case of insect-derived products for human or animal use. Although transgenic silkworms have been generated to produce human therapeutic proteins (4), this technology has not yet been used to produce vaccine antigens. However, genetically modified baculoviruses (*Autographa californica* nuclear polyhedrosis virus and *Bombyx mori* nucleopolyhedrovirus) have been used to generate insect-derived vaccines (insectigens). Basically, the same baculoviruses used for antigen expression in insect cell cultures can be used to infect insect larvae. Upon infection, the recombinant antigen is accumulated in insect tissues and, after 3-4 days of infection, the larvae can be processed to obtain the recombinant antigen in quantities that can reach between several hundreds of µg to several milligrams per infected larva. Experimental vaccines against animal infectious diseases have been tested with very good results, even using nonpurified soluble antigens obtained from larva, without any side effects in animals after repetitive immunization protocols (5, 6, 7, 8). Other proteins with different applications have also been produced in insects as living biofactories, such as enzymes (9, 10), antibodies (11, 12), hormones (13, 14), cytokines (15, 16) and diagnostic proteins (17, 18, 19, 20). Most of these above mentioned proteins were processed correctly after synthesis, and their functional activities remained intact in soluble larval protein extracts. Insects as living biofactories constitute a promising alternative to conventional fermentation technologies and also to plant-derived proteins because of the production versatility, scalability, efficiency and speed of development.

Accelerating recombinant protein expression, so that protein expression takes place before the cellular machinery of insect larvae is severely impaired by the baculovirus infection, would be an important improvement of the BEVS. Late expression, driven by the conventional strong virus promoters of polyhedrin (polh) or p10 genes, has serious disadvantages in the foreign protein post-translational modifications. Baculovirus promoters that allow for earlier expression than the conventionally used polh or p10 promoters have been characterized and been used for heterologous protein production, but showed a reduced productivity (21).

Another possibility for improving the BEVS would be to increase preservation of cell integrity at late times post-infection by reducing the virus-induced cell death. Reduction in the severe impairment of the insect cell machinery at late times post-infection caused by BEVS should not only increase the time frame for producing and accumulating recombinant proteins (secreted or not), but also allow more time for the folding of complex proteins or any post-translational modification of the produced proteins. Baculovirus-infected insect larvae produce and accumulate recombinant proteins during the course of infection and in a virus dose-dependent manner. A prolonged survival of the infected larvae together with a certain protection to high infectious doses would dramatically increase the productivity of insects serving as living biofactories.

Some baculovirus DNA elements have been determined to be involved in the activation of late expression factor genes, which are necessary for virus propagation. One of them is the immediate early (ie) protein IE-1 and its splice variant IE-0 from AcMNPV (*Autographa californica* multinuclear polyhedrosis virus). Translation of the AcMNPV mRNAs encoded by Ac-ie-01 cDNA results in both IE-0 and IE-1 production due to internal translation initiation. Both are thought to be critical mediators of baculovirus gene expression due to their potency as transcriptional regulators (22). Synthesized very early during infection, AcMNPV IE-1 is a 67-kDa dimeric DNA-binding protein that stimulates transcription in plasmid transfection assays through the activity of its N-terminal acidic domain (23, 24). IE-1 accumulates within the nucleus, where it is maintained through late times (25). Transactivation by IE-1 is enhanced by its binding as a homodimer to the baculovirus homologous region (hr) sequences, which function as transcriptional enhancers and origins of viral DNA replication. AcMNPV immediate early protein IE-0 (74 kDa) is identical to IE-1 except for an additional 54 amino acid residues at its N-terminus. AcMNPV IE-0 is a 726-kDa 636 amino acid protein composed of 38 amino acids encoded by orf141 (exon0), 16 amino acids encoded by the upstream nontranslated leader of ie1, and the entire 582 amino acid IE-1 protein. The final product is therefore identical to IE-1 except for the additional 54 amino acids fused to the N-terminus. Presumably due to their common sequences, IE-0 and IE-1 share biochemical activities, including hr enhancer binding and transcriptional regulation.

Given the lack of novel alternative promoters stronger than those commercially used (polh and p10) and of any alternative to implement long-term expression in the baculovirus system by reducing virus-induced cell damage, the present invention is focused on solving said problems by means of the incorporation of recombinant DNA elements in baculovirus expression cassettes. The present invention surprisingly shows that said expression cassettes, containing baculovirus transcriptional regulators, an enhancer homologous region (hr) sequence and a promoter or a combination of promoters are able to increase recombinant protein production to unprecedented levels in insect larvae. Additionally, the expression cassettes of the present invention also increase the survival rate of baculovirus-infected insect larvae at late times post-infection using high infectious doses, thus minimizing the pathogenicity effect in insects caused by the baculovirus infection. On the other hand, an improvement in the integrity of cell functions during baculovirus infection also contributes to the correct recombinant protein posttranslational processing in insect larvae.

SUMMARY OF THE INVENTION

The present invention provides products and methods for the improved expression of recombinant proteins in baculovirus-infected insect larvae.

The following items are preferred embodiments for allowing this improved expression:
1. Insect comprising a nucleic acid sequence that allows for the expression above endogenous levels of the proteins IE-1, IE-0 and/or fragments thereof functioning as transcriptional regulators, wherein the nucleic acid is selected from the group consisting of:
    (a) a nucleic acid containing the nucleotide sequence indicated in any of SEQ ID NO: 2-5;
    (b) a nucleic acid sequence having a sequence identity of at least 70%, preferably at least 75%, more preferably at least 80%, more preferably at least 85%, more preferably at least 90% and most preferably at least 95% with the nucleotide sequence indicated in any of SEQ ID NO: 2-5 and encoding a protein able to function as a transcriptional regulator in a recombinant baculovirus;
    (c) a nucleic acid sequence encoding an amino acid containing the amino acid sequence indicated in any of SEQ ID NO: 6-9; and
    (d) a nucleic acid sequence encoding an amino acid sequence having a sequence similarity of at least 70%, preferably at least 75%, more preferably at least 80%, more preferably at least 85%, more preferably at least 90% and most preferably at least 95% with the amino acid sequence indicated in any of SEQ ID NO: 6-9 and able to function as a transcriptional regulator in a recombinant baculovirus.
2. Insect according to item 1, further comprising at least one recombinant homologous region (hr) as enhancer region, operably linked to any promoter that is suitable for driving the expression of a recombinant protein.
3. Insect according to item 2, wherein the recombinant homologous region (hr) is the sequence indicated in SEQ ID NO: 27 (hr1).
4. Insect according to item 2 or 3, wherein the promoter operably linked to the homologous region (hr) is selected from the group of nucleic acids comprising:
    (a) a nucleic acid containing the nucleotide sequence indicated in any of SEQ ID NO: 10-16; and
    (b) a nucleic acid sequence able to function as a promoter in a recombinant baculovirus and having a sequence identity of at least 70%, preferably at least 75%, more preferably at least 80%, more preferably at least 85%, more preferably at least 90% and most preferably at least 95% with the nucleotide sequence indicated in any of SEQ ID NO: 10-16.
5. Insect according to any of the items 1-4, comprising a nucleic acid sequence that comprises combinations of recombinant promoters, sequences encoding transcriptional regulators and enhancer regions selected from the group comprising SEQ ID NO: 17-26.
6. Insect according to any of the items 1-5, further comprising a nucleic acid sequence encoding a recombinant protein, wherein said nucleic acid sequence is operably linked to a nucleic acid sequence selected from the group consisting of the nucleic acid sequences of items 1-5.
7. Insect according to any one of the items 1-6, wherein the insect is derived from the genus Lepidoptera.
8. Insect according to any of the items 1-7, wherein the insect is selected from the group consisting of *Trichoplusia ni, Spodoptera frugiperda, Spodoptera exigua, Ascalapha odorata, Bombyx mori, Rachiplusia ni* and *Stigmene acrea*.
9. Insect according to any of the items 1-8, wherein the nucleic acid sequence(s) is introduced into the insect by a recombinant baculovirus, preferably AcMNPV or BmNPV.
10. Method for producing a recombinant protein that comprises the use of an insect of any of the items 1-9 and the extraction and purification of the recombinant protein by conventional means.
11. Method for producing a recombinant protein according to item 10, wherein the recombinant protein is selected from the group comprising subunit monomeric vaccine, subunit multimeric vaccine, virus like particle, therapeutic protein, antibody, enzyme, cytokine, blood clotting factor, anticoagulant, receptor, hormone or diagnostic protein reagent.
12. Rearing, feeding or injection medium for an insect comprising the nucleic acid sequence(s) as specified in any of the items 1-6.

BRIEF DESCRIPTION OF THE FIGURES

FIG. 6: A) Percentage of larvae surviving 96 hours post-infection using 5×10$^4$ PFUs as the infectious dose of the baculovirus overexpressing the Ac-ie-01 cDNA under the polh promoter (polhAc-ie-01) or using a conventional baculovirus expressing GFP under the polh promoter (polhGFP) B) Insect biomass at the time of infection with the same baculoviruses as in panel A and the recovered biomass at 96 hours post-infection. The infectious dose was 5×10$^4$ PFUs.

DETAILED DESCRIPTION OF THE INVENTION

Figure 1:
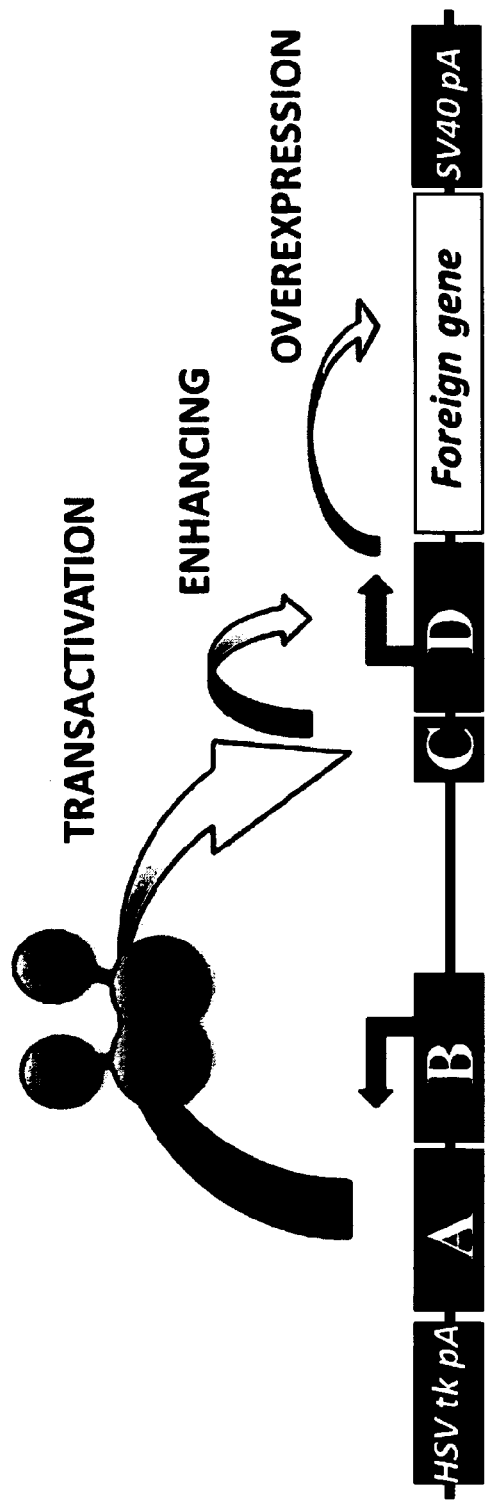
FIG. 1: Schematic representation of the baculovirus recombinant DNA elements of the invention, comprising four principal elements: a sequence encoding for transcriptional regulators (A; e.g. IE0 and IE1), which expression is driven by a promoter (B; e.g. polh or pB2$_9$); an enhancer homologous region (hr) sequence (C; e.g. hr1), upstream of the promoters (D; e.g. p10, pB2$_9$p10 or p6.9p10) driving the expression of the foreign gene coding for the recombinant protein. The scheme shows the theoretical mechanism of interaction between the recombinant DNA elements of the present invention that results in the unprecedented overexpression of the recombinant protein.

The present invention improves the expression of recombinant proteins by means of the introduction of recombinant DNA elements into insects.

These recombinant DNA elements of the present invention are sequences that cause the expression of baculovirus transcriptional regulators above endogenous levels and optionally enhancer homologous regions (hr) and promoters operably linked to these aforementioned elements.

Furthermore, the recombinant DNA elements may form part of an expression cassette.

"Expression cassette" refers to a nucleic acid sequence that contains recombinant DNA elements, which control (e.g. the promoter) and/or are required (e.g. the gene itself) for gene expression. The expression cassette can be introduced in a recombinant vector or baculovirus.

The recombinant DNA elements may be incorporated in a single nucleic acid sequence, cloning vector, transfer vector, recombinant baculovirus or cell. However, they can also be present in different nucleic acid sequences, cloning vectors, transfer vectors or recombinant baculoviruses and be introduced into the same cell.

The present invention surprisingly shows that introduction into insect larvae of sequences that cause the expression of baculovirus transcriptional regulators above endogenous levels and optionally the introduction of an enhancer homologous region (hr) sequence, a promoter or a combination of promoters is able to increase the production of a recombinant protein to unprecedented levels. This indicates the usefulness of this system for the expression of recombinant proteins in vivo.

Additionally, the introduction of these recombinant DNA elements into insect larvae with baculoviruses increases the survival rate of the larvae late after infection, especially after using high virus doses for infection (maximizes the recovered amount of biomass, i.e. the productivity of the system), as compared to larvae infected with a conventional baculovirus. The insect biomass recovered at the end of the production process is significantly increased as well.

Also, the integrity of the molecular cell machinery and cell morphology of said baculovirus-infected larvae is improved as compared to larvae infected with a conventional baculovirus. An improvement in the integrity of cell functions during baculovirus infection also contributes to the correct post-translational processing of the recombinant protein.

Thus, one aspect of the invention relates to an insect that contains a nucleic acid sequence that allows for the expression above endogenous levels of transcriptional regulators. In a preferred embodiment, the transcriptional regulators are IE-1, IE-0 and/or fragments thereof. In a further preferred embodiment, the insect is a transgenic insect.

"Transcriptional regulator" refers to a regulatory protein that has the ability to modulate the transcription of specific genes by, for example, binding to enhancer or repressor regions and/or recruiting further proteins that are involved in transcription.

IE-1 and its splice variant IE-0 are transcriptional regulators that are endogenously expressed during baculovirus infection. According to the present invention, IE-1, IE-0 and/or fragments thereof are recombinantly expressed to increase the total level of these proteins above endogenous levels. This can be achieved through, for example, introducing further copies of the endogenous gene or manipulating the expression of the promoter of the endogenous gene. Further copies of the endogenous genes can be introduced as transgenes under the control of a suitable promoter such as polh or pB2$_9$.

The expression level of the proteins IE-1, IE-0 and/or fragments thereof can be determined at both the mRNA and at the protein level with methods conventionally known to the person skilled in the art, such as quantitative PCR and Western Blot analysis.

According to the invention, IE-1, 1E-0 and fragments thereof are encoded by the nucleic acids of SEQ ID NO: 3 (also referred to as Ac-ie-01) to SEQ ID NO: 5. SEQ ID NO: 3 is the Ac-ie-01 cDNA that encodes both IE-1 and 1E-0, SEQ ID NO: 2 is the coding sequence (CDS) of IE-1 and SEQ ID NO: 3 is the CDS of IE-0. SEQ ID NO: 4 and 5 are the CDSs of the N-terminal domains of IE-1 and 1E-0 respectively that retain the catalytic transcriptional regulator activity. The proteins that are encoded by SEQ ID NO: 2-5 are represented by SEQ ID NO: 6-9 respectively.

The present invention furthermore discloses variants of SEQ ID NO: 2-9 that are or encode amino acids that are able to function as a transcriptional regulator. These variants are nucleic or amino acids whose nucleotide or amino acid sequence differs in one or more positions from these parental nucleic or amino acids, whereby differences might be additions, deletions and/or substitutions of nucleotides or amino acid residues.

Nucleic and amino acid sequences of the present invention shall be distinguished from other nucleic and amino acid sequences by their degree of sequence identity or similarity respectively as determined using EMBOSS Needle with the default parameters. Methods for the generation of such variants include random or site directed mutagenesis, site-saturation mutagenesis, PCR-based fragment assembly, DNA shuffling, homologous recombination in vitro or in vivo, and methods of gene-synthesis.

The sequence of the variants of SEQ ID NO: 2-5 is at least 70%, preferably at least 75%, more preferably at least 80%, more preferably at least 85%, more preferably at least 90% and most preferably at least 95% identical to the sequences of SEQ ID NO: 2-5.

The sequence of the variants of SEQ ID NO: 6-9 is at least 70%, preferably at least 75%, more preferably at least 80%, more preferably at least 85%, more preferably at least 90% and most preferably at least 95% similar to the sequences of SEQ ID NO: 6-9.

The insect is preferably a lepidopter and more preferably an insect selected from the group consisting of *Trichoplusia ni*, *Spodoptera frugiperda*, *Spodoptera exigua*, *Ascalapha odorata*, *Bombyx mori*, *Rachiplusia ni* and *Stigmene acrea*. In a preferred embodiment, the insect is a larva.

In a preferred embodiment, the insect of the present invention further contains, in addition to the nucleic acid sequence that allows for the expression above endogenous levels of the proteins IE-1, IE-0 and/or fragments thereof, a recombinant homologous region (hr) that can enhance the expression of a recombinant protein by being operably linked to the respective promoter.

Homologous regions, hr, are comprised of repeated units of about 70-bp with an imperfect 30-bp palindrome near their center. Homologous regions are repeated at eight locations in the AcMNPV genome with 2 to 8 repeats at each side. Homologous regions have been implicated as both transcriptional enhancers and origins of baculovirus DNA replication.

"Enhancer region" refers to a control sequence, whose binding by transcriptional regulators increases the level of transcription of associated genes.

"Recombinant protein" refers to a protein that originates from recombinant DNA. Such proteins can be used for the benefit of humans and animals and may have industrial, commercial or therapeutic application.

"Being operably linked" refers to two nucleic acid sequences that are connected in a way that one influences the other in terms of, for example, transcriptional regulation.

"Promoter" refers to a DNA sequence to which RNA polymerase can bind to initiate transcription. The sequence may further contain binding sites for various proteins that regulate transcription, such as transcription factors. The promoter sequence may be composed of different promoter fragments (either different or the same fragments) that are localized closely in the DNA sequence and may be separated by linkers or spacer. Such promoters are referred to as chimeric promoters.

The enhancer homologous region sequence hr upstream of the promoter/s is preferably hr1 (SEQ ID NO: 27). The promoters that drive the expression of the recombinant protein are preferably selected from the group comprising SEQ ID NO: 10-16 or a sequence that is able to function as a promoter and has at least 70%, preferably at least 75%, more preferably at least 80%, more preferably at least 85%, more preferably at least 90% and most preferably at least 95% identity with the nucleotide sequence indicated in any of SEQ ID NO: 10-16.

In a preferred embodiment, the nucleic acid sequence comprises combinations of recombinant promoters, sequences encoding transcriptional regulators and enhancer regions selected from the group comprising SEQ ID NO: 17-26.

As indicated above, the recombinant promoters, sequences encoding transcriptional regulators and enhancer regions of the present invention do not need to form part of a single molecule, instead these sequences may form part of distinct molecules as long as they are operably linked, i.e. contained within the same cells.

The insect of the present invention preferably comprises a nucleic acid sequence encoding a recombinant protein. This nucleic acid sequence is operably linked to the nucleic acid sequence that allows for the expression above endogenous levels of the proteins IE-1, IE-0 and/or fragments thereof and optionally to a homologous region (hr).

The above described recombinant DNA elements are preferably introduced into the insect by a recombinant baculovirus. Preferably, the baculovirus is AcMNPV or BmNPV and the insect an insect larva. The baculovirus is administered to the larva by oral administration (per as) or more preferably by injection. In a further embodiment the insect is infected, transfected, transduced or transformed with the recombinant baculovirus, transfer vector, cloning vector or nucleic acid sequence of the present invention. Preferably, the insect larvae are reared in a rearing module, such as described in the patent application ES 2 232 308.

In a further aspect, the invention discloses methods for producing a recombinant protein using the insect of the present invention. To this end, an insect can be infected, transfected, transduced or transformed with the recombinant baculovirus, transfer vector, cloning vector or nucleic acid sequence of the present invention. After expression of the recombinant protein, extraction and purification of the recombinant protein is done by conventional means.

In a preferred embodiment for protein production, the larvae are infected by injecting a high virus dose (higher than 10 Plaque Forming Units) of the recombinant baculovirus of the invention. 3-4 days after infection, the infected larvae are processed and the whole soluble protein extract is obtained by the use of appropriate extraction buffers. Extracts are centrifuged and the lipid fraction eliminated. Then, the recombinant protein is purified by conventional means.

The recombinant protein that is preferably produced by the methods of the present invention is a protein selected from the group comprising subunit monomeric vaccine, subunit multimeric vaccine, virus like particle, therapeutic protein, antibody, enzyme, cytokine, blood clotting factor, anticoagulant, receptor, hormone or diagnostic protein reagent.

One aspect of the invention relates to the use of the recombinant baculovirus, transfer vector, cloning vector or nucleic acid sequence of the invention in a rearing, feeding or injection medium for an insect.

The present invention discloses a baculovirus that can be used to produce the insect of the present invention and comprises said sequence for expression above endogenous levels of the proteins IE-0, IE-1 and/or fragments thereof.

"Baculovirus" refers to a family of infectious viruses for invertebrates, mainly infecting insects and arthropods. A "recombinant baculovirus" has further introduced recombinant DNA through, for example, homologous recombination or transposition. The recombinant baculovirus preferably originates from AcMNPV (*Autographa californica* nuclear polyhedrosis virus) or BmNPV (*Bombyx mori* nucleopolyhedrovirus).

"Recombinant DNA" refers to a form of artificial DNA that is engineered through the combination or insertion of one or more DNA strands, thereby combining DNA that would normally not occur together.

"Recombinant DNA element" refers to a functional element within recombinant DNA, such as a promoter, enhancer or a gene. As mentioned above, the recombinant DNA elements of the present invention are sequences that cause the expression of baculovirus transcriptional regulators above endogenous levels, enhancer homologous regions (hr) and promoters operably linked to these aforementioned elements. Preferably, the baculovirus transcriptional regulators IE-1, IE-0 or fragments thereof are expressed above endogenous levels.

The recombinant baculovirus preferably contains in addition to (i) the sequence for expression above endogenous levels of the proteins IE-0, IE-1 and/or fragments thereof, (ii) a recombinant homologous region (hr) linked to (iii) a suitable promoter for driving the expression of a recombinant protein. The preferred combinations of these recombinant DNA elements are as described above for the insects. Furthermore, the recombinant baculovirus preferably contains a nucleic acid sequence encoding a recombinant protein.

The present invention discloses a transfer vector that can be used to produce the insect and/or recombinant baculovirus of the present invention and comprises said sequence for expression above endogenous levels of the proteins IE-0, IE-1 and/or fragments thereof, in addition to a sequence suitable for integration or transposition in a baculovirus.

Transfer vectors generally permit the insertion of genetic information into a baculovirus.

The transfer vector preferably contains in addition to (i) the sequence for expression above endogenous levels of the proteins IE-0, IE-1 and/or fragments thereof, (ii) a recombinant homologous region (hr) linked to (iii) a suitable promoter for driving the expression of a recombinant protein. The preferred combinations of these recombinant DNA elements are as described above for the insects.

In one preferred aspect, the transfer vector comprises a nucleic acid sequence encoding said recombinant protein, whereas in another preferred embodiment the transfer vector lacks such sequence.

In a preferred embodiment, the transfer vector is a bacmid.

"Bacmid" refers to a plasmid construct which contains the DNA sequence sufficient for generating a baculovirus when transfected into a cell.

In a further preferred embodiment, the transfer vector is derived from any of the commercially available baculovirus expression systems "Bac-to-Bac®" (Invitrogen™), "BacPAK™" (Clontech™), "FlashBAC™" (Oxford Expression Technologies™), "BacuVance™" (GenScript™), "Bac-N-Blue DNA™" (Invitrogen™), "BaculoDirect™" (Invitrogen™), "BacVector®" 1000, 2000, 3000 (Novagen®), "DiamondBac™" (Sigma-Aldrich®) or "BaculoGold™" (BD Biosciences™).

The present invention discloses a cloning vector that can be used to produce the insect, recombinant baculovirus and/or transfer vector of the present invention and comprises said sequence for expression above endogenous levels of the proteins IE-0, IE-1 and/or fragments thereof, which is further suitable for bacterial replication.

"Cloning vector" refers to any vector that is suitable for cloning, which generally involves the presence of restriction sites, an origin of replication for bacterial propagation and a selectable marker.

The cloning vector preferably contains in addition to (i) the sequence for expression above endogenous levels of the proteins IE-0, IE-1 and/or fragments thereof, (ii) a recombinant homologous region (hr) linked to (iii) a suitable promoter for driving the expression of a recombinant protein. The preferred combinations of these recombinant DNA elements are as described above for the insects.

In one preferred aspect, the cloning vector comprises a nucleic acid sequence encoding said recombinant protein (also referred to as the "donor vector"), whereas in another preferred embodiment the cloning vector lacks such sequence.

The present invention discloses a nucleic acid sequence that can be used to produce the insect, recombinant baculovirus, transfer vector and/or cloning vector of the present invention and comprises said sequence for expression above endogenous levels of the proteins IE-0, IE-1 and/or fragments thereof.

The nucleic acid sequence preferably contains in addition to (1) the sequence for expression above endogenous levels of the proteins IE-0, IE4 and/or fragments thereof, (ii) a recombinant homologous region (hr) linked to (iii) a suitable promoter for driving the expression of a recombinant protein. The preferred combinations of these recombinant DNA elements are as described above for the insects.

Its one preferred aspect, the nucleic acid sequence comprises a nucleic acid sequence encoding said recombinant protein, whereas in another preferred embodiment the nucleic acid sequence lacks such sequence.

SUMMARY OF SEQUENCES

| SEQ ID NO: | Name: |
|---|---|
| 3 | Complete Ac-ie-01 cDNA |
| 2 | Protein coding sequence (CDS) of IE-1 |
| 3 | CDS of IE-0 |
| 4 | CDS of the IE-1 N-terminal domain |
| 5 | CDS of the IE-0 N-terminal domain |
| 6 | IE-1 protein |
| 7 | IE-0 protein |
| 8 | IE-1 N-terminal domain protein |
| 9 | IE-0 N-terminal domain protein |

-continued

SUMMARY OF SEQUENCES

| SEQ ID NO: | Name: |
|---|---|
| 10 | polh (promoter) |
| 11 | p10 (promoter) |
| 12 | pB2$_9$p10 (promoter) |
| 13 | p6.9p10 (promoter) |
| 14 | pB2$_9$ (promoter) |
| 15 | pB2p10 (promoter) |
| 16 | polhp10 (promoter) |
| 17 | polhAc-ie-01/hr1p10 |
| 18 | polhAc-ie-01/hr1pB2$_9$p10 |
| 19 | polhAc-ie-01/hr1p6.9p10 |
| 20 | pB2$_9$Ac-ie-01/hr1p10 |
| 21 | pB2$_9$Ac-ie-01/hr1pB2$_9$p10 |
| 22 | pB2$_9$Ac-ie-01/hr1p6.9p10 |
| 23 | polhAc-ie-01/hr1polh |
| 24 | pB2$_9$Ac-ie-01/hr1polh |
| 25 | polhAc-ie-01/hr1polhp10 |
| 26 | pB2$_9$Ac-ie-01/hr1polhp10 |
| 27 | Homologous region enhancer hr1 |
| 28 | polhAc-ie-01 |
| 29 | polhGFP |

Deposition of Microorganisms According to the Budapest Treaty

Plasmids were deposited in the Spanish Type Culture Collection (CECT) (www.cect.org); University of Valencia, Parc Científic Universitat de València; Catedrático Agustin Escardino, 9; 46980 Paterna (Valencia), Spain, with the accession number CECT 8031, on the date Oct. 4, 2011.

EXAMPLES

Example 1. Overexpression of Baculovirus Transcriptional Regulators Potentiates the Enhancer Function of a Homologous Region hr Functionally Linked to a Promoter Increasing Recombinant Protein Expression in a Baculovirus Vector Expression System (BEVS)

Immediate early viral proteins encoded by the Ac-ie-01 cDNA, i.e. IE-1 and IE-0, from AcMNPV are potent transcriptional regulators in baculoviruses. Transactivation mediated by these proteins is enhanced by their binding as a homodimer to the baculovirus homologous region (hr) sequences, which act as transcriptional enhancers. AcMNPV IE-1/IE-0 are 67-72 kDa dimeric DNA-binding proteins that stimulate transcription in plasmid transfection assays through the activity of their N-terminal acidic domain (7, 8). Synthesized very early during infection, IE-1 and IE-0 accumulate within the nucleus, where they are maintained through late times. Using the dual plasmid pFastBac™ (Invitrogen™), the Ac-ie-01 cDNA was cloned under the control of the polh promoter. In the same plasmid, but in another locus, the GFP encoding gene was cloned downstream of the hr1p6.9p10 chimeric promoter that was previously synthesized and contains the homologous region hr1 fused to the promoters p6.9 and p10. A schematic representation of the resulting baculovirus expression cassette of the present invention and the putative function of the recombinant DNA elements is shown in FIG. 1. The resulting plasmid was used to generate a recombinant baculovirus by the "Bac-to-Bac®" system (Invitrogen™). In parallel, a conventional baculovirus expressing the GFP protein under the control of polh promoter was generated by the same system.

The expression of GFP protein mediated by the different baculoviruses was studied by fluorimetry at 96 hours post-infection in *Trichoplusia ni* larvae using a low or high infectious dose ($5 \times 10^2$ or $5 \times 10^4$ respectively). The expression level of GFP was increased in larval extracts by the baculovirus containing above expression cassette of the present invention by about 13 to more than 40% depending on the virus dose used (FIG. 4A). Similar results were observed by using baculoviruses in which the Ac-ie-01 cDNA was expressed under the control of the insect-derived pB2$_9$ promoter or when the GFP was expressed under the control of the hr1pB2$_9$p10 promoter (data not shown).

Figure 4:
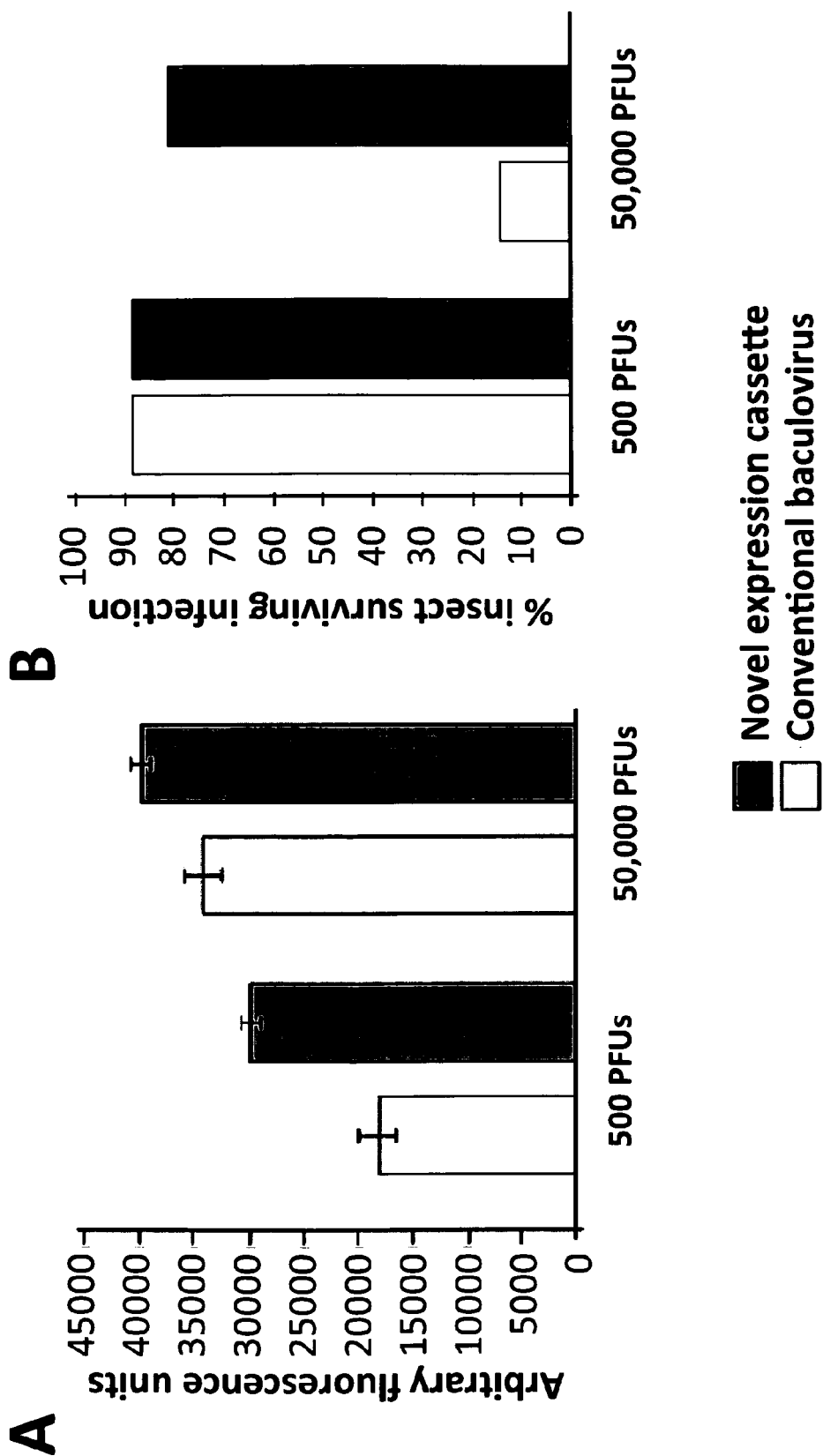
FIG. 4: A) Recombinant GFP production 96 hours post-infection in Trichoplusia ni insect larvae (fifth instar) inoculated with 500 or 50,000 PFUs of a conventional baculovirus expressing the protein under the control of the polh promoter or by a baculovirus containing the baculovirus cassette of the invention polh Ac-ie-01/hr1p6.9p10GFP. B) Percentage of larvae surviving 96 hours post-infection with the same baculoviruses as in panel A and at two different infectious doses, i.e. 500 and 50,000 PFUs.

Example 2. The Baculovirus Expression Cassettes of the Invention Increase the Baculovirus-Infected Insect Larvae Surviving Rates and Insect Biomass Recovered Using High Infectious Doses Through the Transcriptional Regulators Encoded by the Ac-ie-01 cDNA In the previous example an advantage of baculoviruses expressing the recombinant protein in the context of the baculovirus cassette of the present invention in terms of protein productivity was shown. However, the main difference observed was in respect to the percentage of surviving larvae at high infectious doses (maximum productivity). Under such infection conditions, the baculovirus containing the expression cassette of the present invention increased by about 70% the larvae survival rates (FIG. 4B). This means that by using a conventional baculovirus the optimal infection conditions were using an infectious dose of $5 \times 10^2$ PFUs (maximum larvae surviving rate). In contrast, by using a baculovirus containing the expression cassette of the present invention, a dose of $5 \times 10^4$ could be used, recovering the same number of larvae at the end of the production process (FIG. 4B). Under such optimal production conditions (infection with $5 \times 10^4$ PFUs), the baculovirus containing the expression cassette of the present invention yields more than twice the amount of recombinant protein produced in insect larvae infected with the optimal dose for the conventional baculovirus ($5 \times 10^2$ PFUs) (FIGS. 4 A and B).

Figure 5:
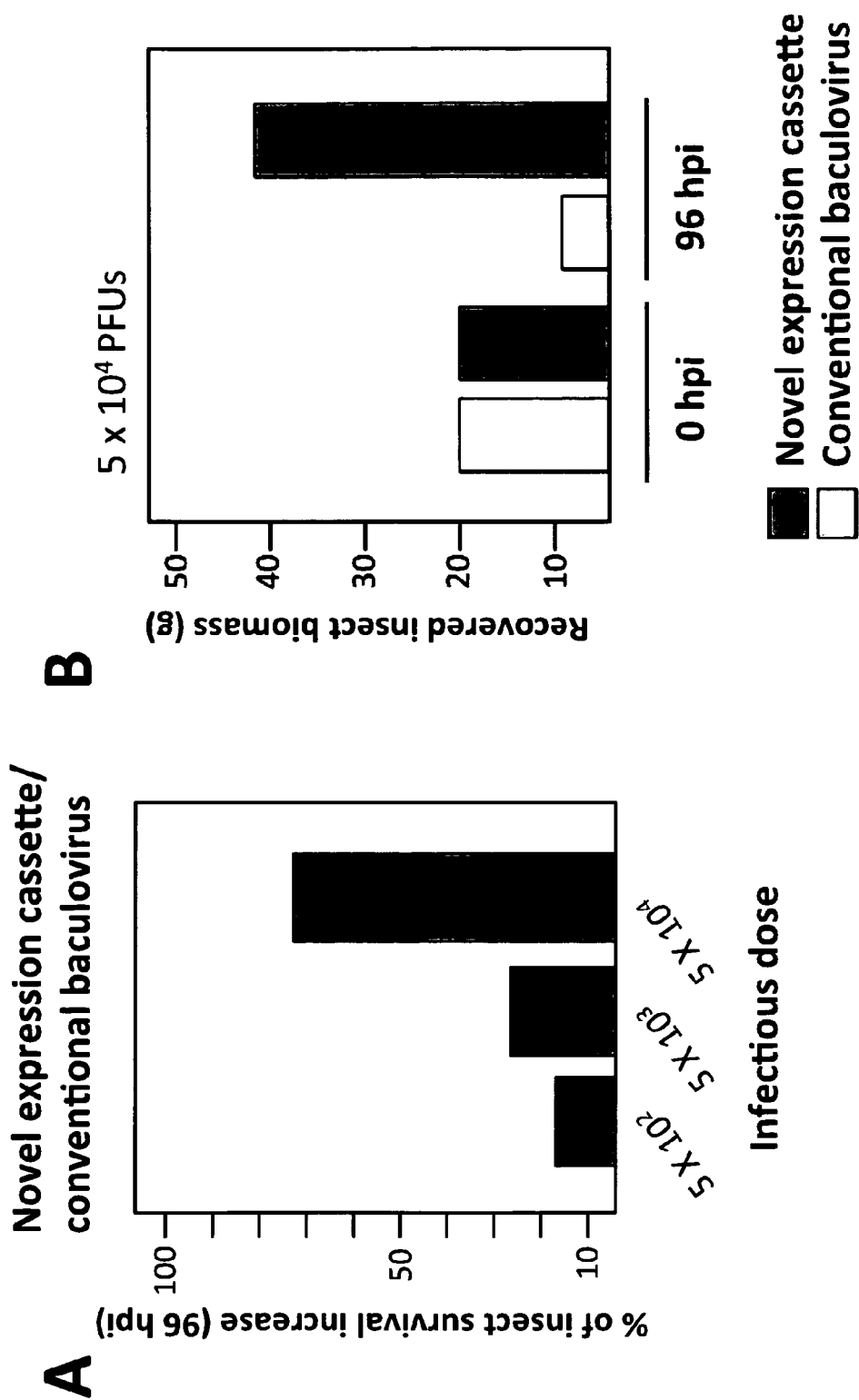
FIG. 5: A) Percentage of larvae surviving 96 hours post-infection with the baculovirus containing the expression cassette of the present invention polhAc-ie-01/hr1p6.9p10GFP with respect to a conventional baculovirus (polhGFP) at different infectious doses. B) Insect biomass at the moment of infection with a conventional baculovirus (polhGFP) or with a baculovirus containing the expression cassette of the present invention (polhAc-ie-01/hr1p6.9p10GFP) and the recovered biomass 96 hours post-infection. The infectious dose was 5×10$^4$ PFUs.

Larvae infection studies using different infectious doses of a conventional baculovirus (polhGFP) or a baculovirus containing the expression cassette of the present invention polhAc-ie-01/hr1p6.9p10GFP, both expressing the GFP protein, revealed increasing surviving rates of infected larvae when the baculovirus containing the expression cassette of the present invention was used (FIG. 5A). At the highest infectious dose ($5 \times 10^4$) the survival rate of larvae infected with the expression cassette of the present invention increased by more than 70% as compared to larvae infected with a conventional baculovirus. This increase in infected larvae surviving rates had direct dramatic consequences in the insect biomass recovered at the end of the production process, with a 80% increase when the baculovirus containing the expression cassette of the present invention was used at the highest infectious dose (maximum productivity) (FIG. 5B).

Figure 6:
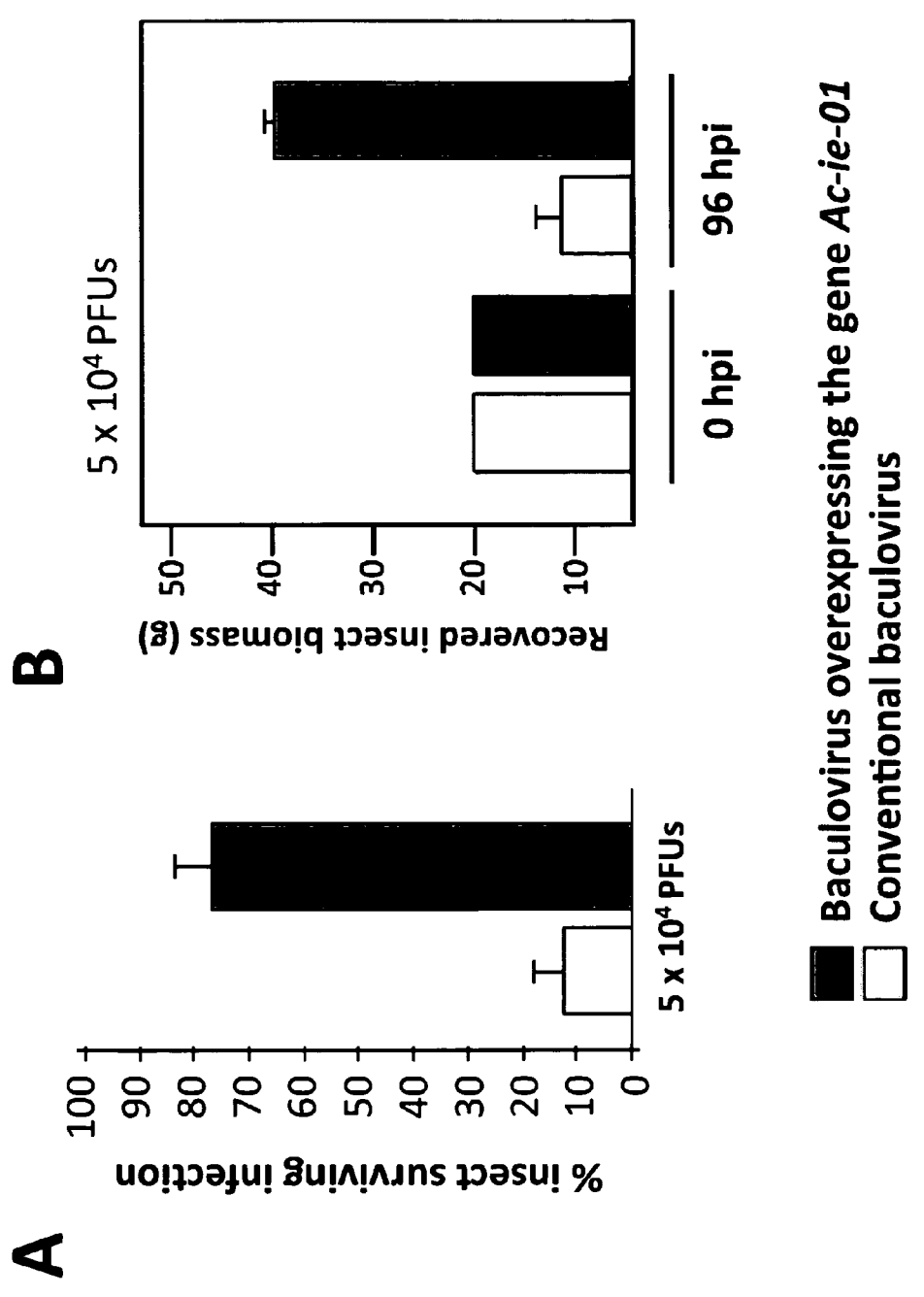

To determine the genetic element/s responsible for such interesting properties related to the increase of survival rates after infection with high doses of the baculovirus of the invention, a recombinant baculovirus expressing the transcriptional regulators encoded by the Ac-ie-01 cDNA under the control of the polh promoter was generated. Then, *T. ni* larvae were infected with a high infectious dose ($5 \times 10^4$ PFUs) of this baculovirus. As control, we used a baculovirus expressing the GFP protein under the control of the same promoter. Similarly to the larvae infected with the expression cassette of the present invention polhAc-ie-01/hr1p6.9p10GFP, larvae infected with the baculovirus overexpressing the Ac-ie-01 cDNA (polhAc-ie-01) also showed increased survival rates when compared with larvae infected with a conventional baculovirus expressing the GFP reporter protein under the control of the same promoter (polhGPF) (FIG. 6A). This strongly suggests that the overexpression of the transcriptional regulators used in the baculovirus expression cassette of the present invention protects the insect larvae from the baculovirus-induced mortality, allowing long-term expression (more recombinant protein production) and increasing the insect biomass recovery using high infectious doses (maximum productivity) (FIG. 6B).

Example 3. Overexpression in a Baculovirus Expression System of Transcriptional Regulators Encoded by the Ac-ie-01 cDNA Facilitates the Post-Translational Processing of Recombinant Proteins in Infected Insect Larvae Used as Biofactories Cellular integrity during baculovirus infection is of great importance to ascertain the correct folding or any other post-translational modification of foreign proteins expressed by this system. The baculovirus strong promoters commonly used for research and production, such as polh and p10, only express the foreign genes at late times post-infection when infected cells already show severe cytopathic effects and the cellular viability decreases. As described above, the overexpression of the transcriptional regulators used in the baculovirus expression cassette of the present invention protects cells from pathogenic effects of the baculovirus infection, allowing a wide temporal window for recombinant protein production in cells remaining fully viable.

The relevance of the recombinant DNA elements incorporated into the expression cassette of the invention in relation to post-translational modifications of recombinant proteins in insect larvae as living biofactories was studied. For this purpose, a conventional baculovirus expressing the reporter protein GFP under the control of the polh promoter and a baculovirus incorporating the baculovirus cassette of the present invention and also expressing the GFP protein (polhAc-ie-01/hr1p6.9p10GFP) were used to infect insect larvae at a dose of $5 \times 10^4$ PFUs.

Figure 7:
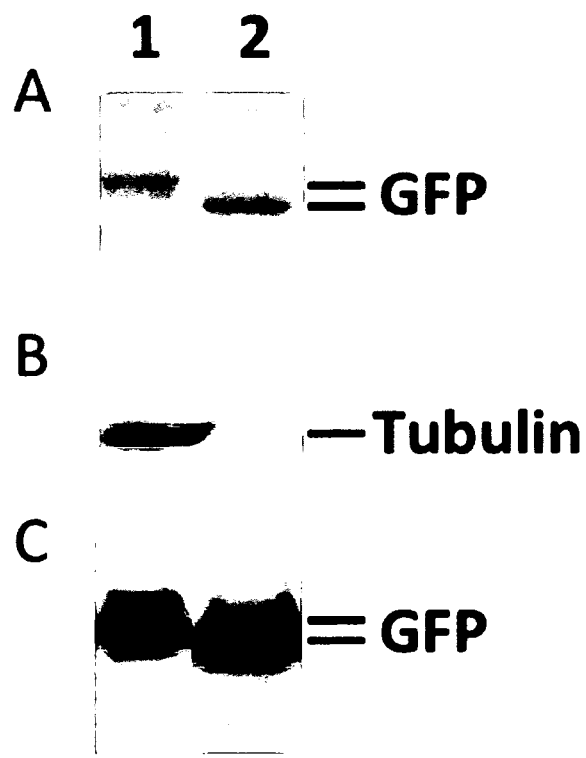
FIG. 7: Comparison of the recombinant GFP protein expressed by a conventional baculovirus under the control of the polh promoter (2) or by a baculovirus containing the expression cassette of the present invention polhAc-ie-01/hr1p6.9p10GFP (1). Extracts from larvae infected with 5×10$^5$ PFUs of every baculovirus were obtained 96 hours post-infection. A) Coomassie blue staining of the recombinant GFP protein. B) Cell integrity after baculovirus infection determined by tubulin detection with a specific antiserum. C) Western blot detection of recombinant GFP protein by using a specific anti-GFP serum.

Infected larvae extracts were analysed at 96 hours post-infection by SDS-PAGE gels and Coomassie blue staining (FIG. 7A). Interestingly, GFP protein expressed by a conventional baculovirus showed a band with a reduced molecular weight (lower than predicted), suggesting degradation or misfolding of the recombinant protein. In contrast, when the GFP protein expression was mediated by the baculovirus expression cassette of the present invention, the GFP band presented the expected molecular weight of this protein, i.e. about 27 kDa.

The infected larvae extracts were also analyzed by Western blot using anti-GFP monoclonal antibody (mab2515; Millipore™) (FIG. 7C). The GFP protein was detected in larvae extracts infected by both baculoviruses, but showed a difference in electrophoretic mobility of the recombinant protein as observed by Coomassie blue staining.

In parallel, the integrity of the cell machinery was measured at different times post-infection by Western blot analysis of the cellular tubulin protein using a specific antiserum (FIG. 7B). Infection with a conventional baculovirus impaired severely the cell integrity at 96 hours post-infection since the tubulin band detected decreased dramatically after this time point (degradation as a result of a complete loss of cell integrity). Consistent with the cellular protection induced by the recombinant DNA elements contained in the baculovirus expression cassette of the invention, cellular tubulin was not equally affected in cells infected by the recombinant baculovirus engineered with the expression cassette.

Example 4. Cell Culture and Viruses

Figure 8:
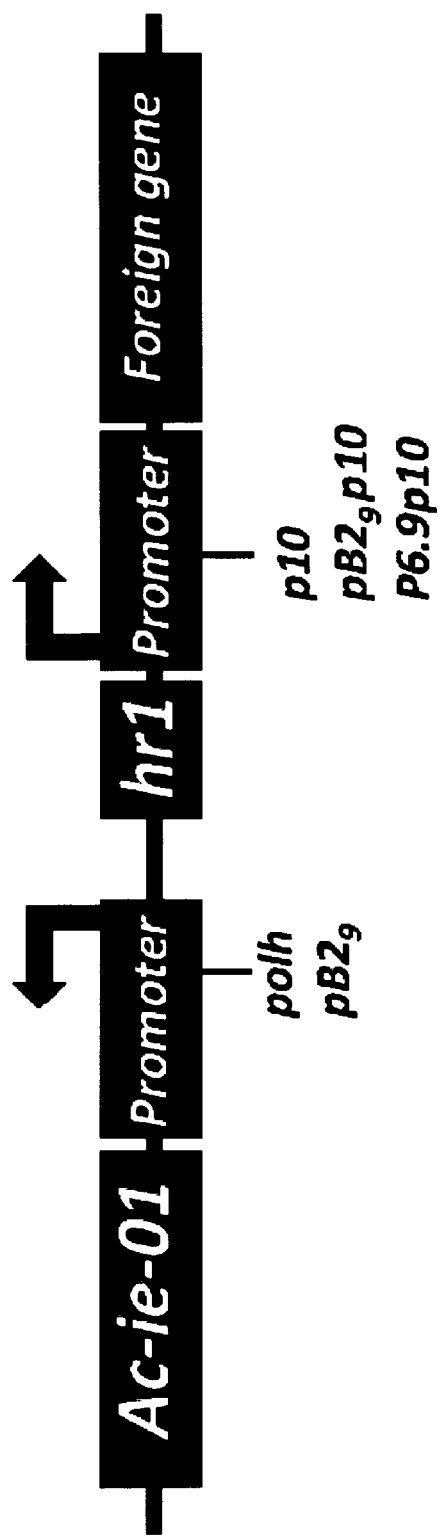
FIG. 8: Schematic representation of the preferred elements contained in the baculovirus expression cassettes of the invention, comprising encoding sequences for transcriptional regulators, homologous regions (hr) enhancing the transcription induced by promoter(s) of a foreign gene encoding a recombinant protein.

The *Spodoptera frugiperda* Sf21 or Sf9 cell lines were cultured in 6-well tissue culture plates ($1 \times 10^6$ cells/well) in TNM-FH insect medium (Pan Biotech™, Germany) containing 10% heat-inactivated fetal bovine serum (Pan Biotech™, Germany) at 27° C. AcMNPV recombinant baculoviruses were obtained by the "Bac-to-Bac®" Baculovirus Expression System (Invitrogen™, USA). Different transfer vectors containing the recombinant DNA elements of the invention were generated using the pFastBac™-DUAL plasmid (Invitrogen™). The promoters and regulatory elements incorporated into pFastBac™-DUAL were synthesized (GenScript™, USA) with the adequate flanking restriction sequences to facilitate the cloning. These transfer vectors were used to transfect Sf21 cells with Cellfectin® (Invitrogen™, USA). The resulting recombinant baculoviruses from the infection of Sf21 cells were then passaged twice in cells and titered by the plaque assay method. The obtained gene constructs of the baculovirus expression cassettes are schematically shown in FIG. 8, showing different potential combinations of promoters driving the expression of the Ac-ie-01 cDNA or the foreign gene (e.g. GFP). The different expression cassettes were used to generate the recombinant baculoviruses used in the examples shown in FIGS. 4 to 7.

Example 5. Generation of the Cloning Vector

The cloning vector is a small piece of DNA containing the baculovirus expression cassette of the present invention into which a foreign DNA fragment can be inserted by treating the vehicle and the foreign DNA with a restriction enzyme that creates the same overhang, then ligating the fragments together. The essential characteristics of the cloning vector must include a synthetic multiple cloning site (MCS) to facilitate the insertion of foreign genes directed in a chosen orientation, a selectable marker, such as an antibiotic resistance to allow the selection of positively transformed cells and a functional origin of replication (ORI) for propagation in bacteria.

Example 6. Generation of the Donor Vector Containing the Baculovirus Expression Cassette of the Present Invention A donor vector consists of a cloning vector, for example a pUC57 plasmid, containing the baculovirus expression cassette, into which a foreign gene has been cloned using the appropriate restriction enzymes. The baculovirus expression cassette of the present invention was synthesized by ligating the following DNA sequences: (i) the baculovirus transcriptional regulator encoding sequence Ac-ie-01 downstream of a promoter sequence, such as the polh or the pB2$_9$ promoter, and upstream of the HSV TK polyadenylation signal and (ii) in another locus an enhancer sequence, for example, the homologous region hr1, upstream of (iii) a promoter sequence, for example, pB2$_9$p10, p10, p6.9p10 or polh, followed by a multiple cloning site (MCS) for cloning the gene of interest and the SV40 polyadenylation signal downstream of the MCS (FIG. 1). The baculovirus expression cassette is flanked by specific restriction sites (for example BglII and BstZ17I at the 5'-terminal end and Bgl II and Sgf I at the 3'-terminal end) to facilitate subcloning into a transfer vector of a commercial baculovirus generation system (based on transposition, for example the "Bac-to-Bac®" system (Invitrogen™), or based on homologous recombination, for example "flashBACT™" (Oxford Expression Technologies™), "Baculogold™" (BD Biosciences™), "BacPAK6™" (Clontech™), "Bac-N-Blue DNA™" (Invitrogen™)) (FIGS. 2 and 3).

Figure 2:
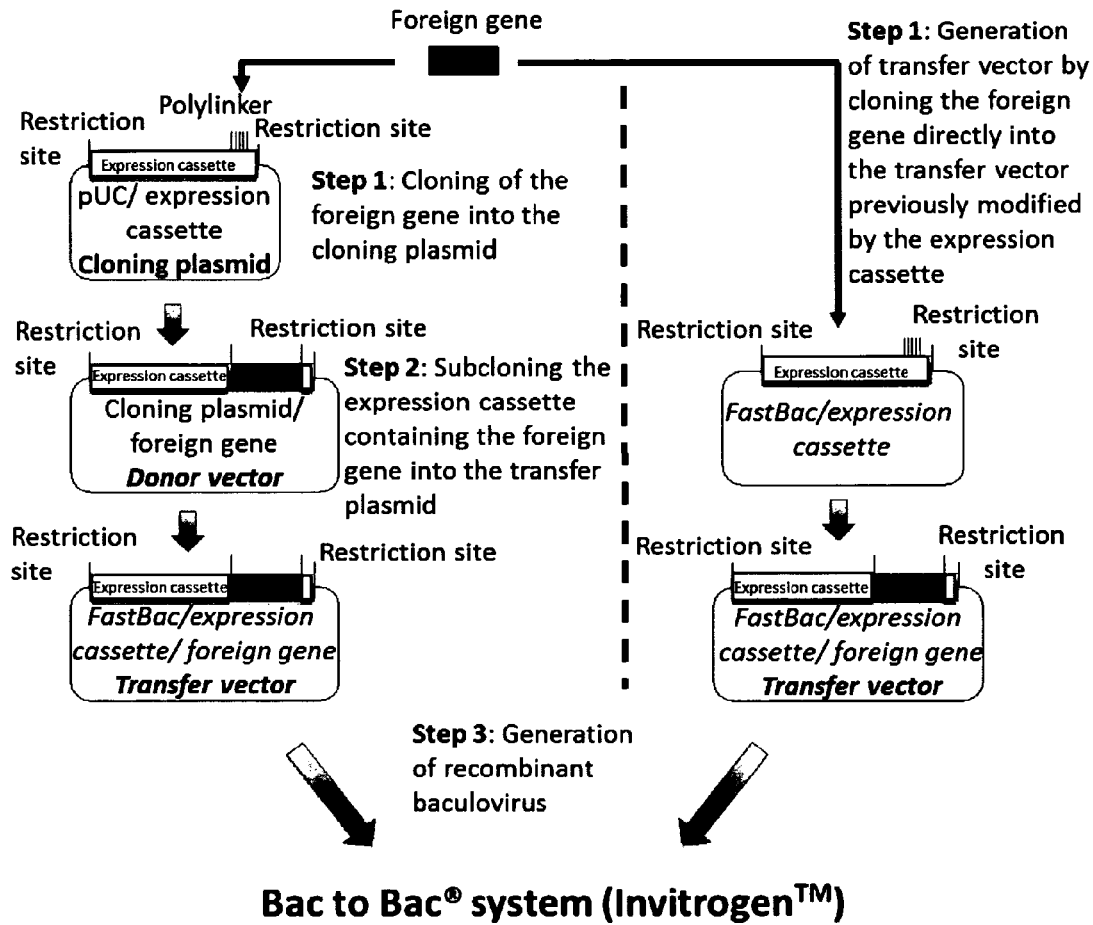
FIG. 2: Different strategies that result in the generation of recombinant baculoviruses by the "Bac-to-Bac®" cloning system (Invitrogen™).
Figure 3:
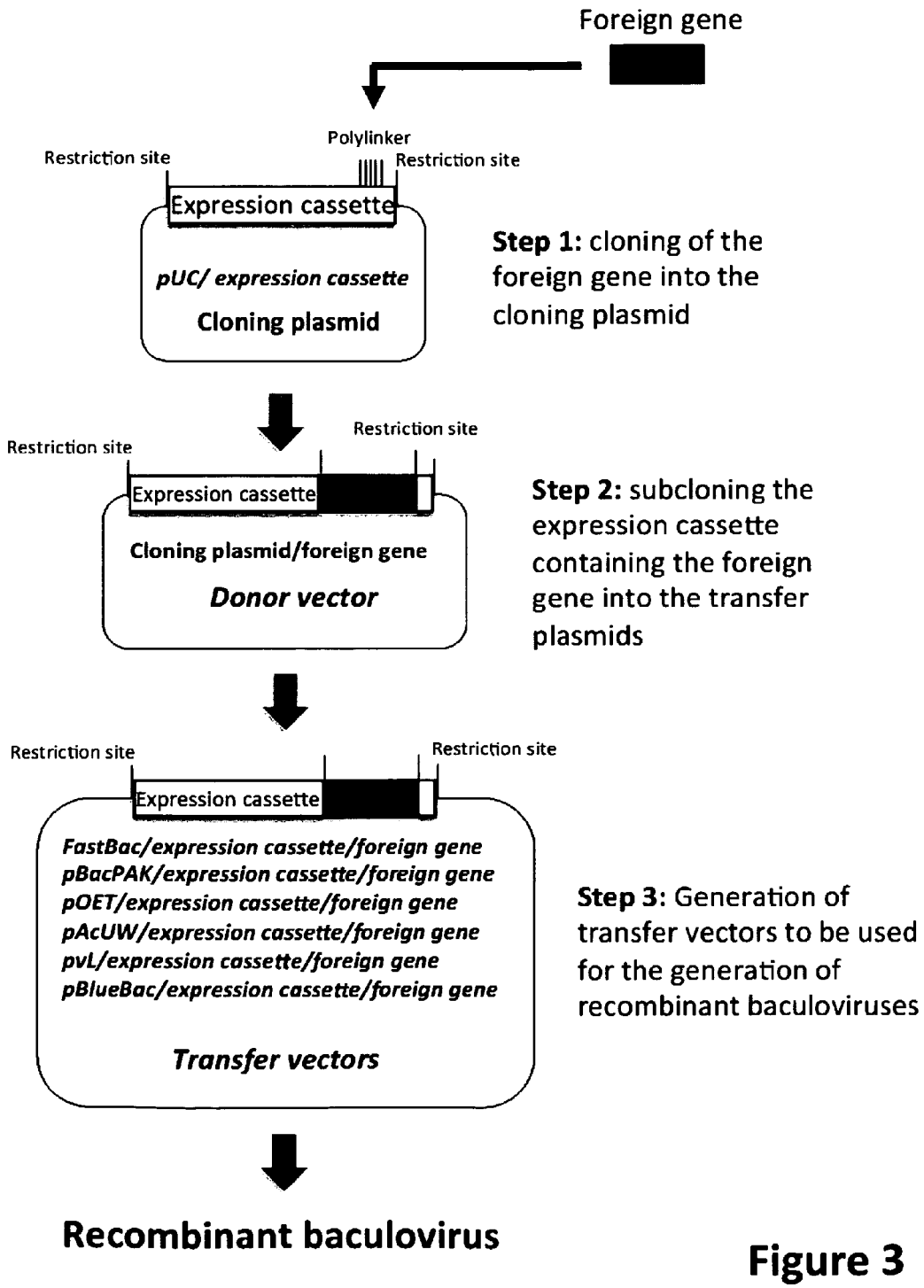
FIG. 3: General scheme for the generation of cloning, donor and transfer vectors compatible with other commercial technologies used to generate recombinant baculoviruses.

The encoding gene of the Green Fluorescence Protein (GFP) was cloned into the MCS of the cloning vector using the Nco I and Spe I restriction sites, generating the donor plasmid vector (FIG. 2).

Example 7. Generation of the Transfer Vector Containing the Baculovirus Expression Cassette of the Present Invention The transfer vector was generated by digesting a donor vector with BstZ17 I of the 5'-flanking site and with Xha I and cloning it into the transfer vector pFastBac™1 that was also digested with the same enzymes. In this case, as a result of the subcloning, the SV40 polyadenylation signal of the baculovirus expression cassette is exchanged by the SV40 polyadenlation signal from the transfer vector. Apart from this, all the elements of the expression cassette are included in the pFastBac transfer vector, substituting the polh promoter and MCS of the original commercial transfer vector (FIG. 2).

Example 8. Generation of the Baculovirus Expression Vector Containing the Baculovirus Expression Cassette of the Present Invention Using the "Bac-to-Bac®" System The modified transfer vector pFastBac™1 and the individual baculovirus expression cassette were used to generate a recombinant baculovirus by using the "Bac-to-Bac®" Baculovirus Expression System. More specifically, the modified transfer vector was used to transform the *E. coli* host strain DH10Bac™ that contains a baculovirus shuttle vector (bacmid) and a helper plasmid, and allows the generation of a recombinant bacmid following transposition of the expression cassette. The DNA of the recombinant bacmid containing the baculovirus expression cassette of the present invention and the GFP encoding gene was then used to transfect insect cells, for example, Sf21 cells, using Cellfectin®. 72 hours post-transfection, cells were harvested and the first recombinant baculovirus generation was obtained (FIG. 2). This recombinant baculovirus could then be further amplified and/or titered following conventional protocols. Similar procedures can be used to generate recombinant baculoviruses with other transfer vectors provided by commercial BEVSs (FIG. 3).

Example 9. Rearing and Infection of Insect Larvae

*Trichoplusia ni* (cabbage looper) larvae were reared under level 2 biosafety conditions. Eggs were placed into specially designed larva developmental cages containing an artificial insect diet and were kept in growth chambers at 22° C. under controlled humidity (50%) and light period (8 h/day) conditions.

Fifth-instar larvae (last instar larvae before pupation), were used for all infection experiments. The standard weight of each larva was approximately 120-130 mg and larvae were injected near the proleg (forward of the body cavity) with 5 μl of recombinant baculoviruses diluted to reach the number of plaque forming units (PFU) per dose selected. Larvae were processed at 96 hpi. The larvae collected were frozen immediately to be stored at −20° C. until they were processed for recombinant protein quantification. Total soluble, non-denatured proteins (TSNDPs) from frozen *T. ni* larvae infected by the baculoviruses were obtained by homogenization using a Bag Mixer® blender (Interscience™, France) for 2 min. Extraction buffer was composed of PBS 1×, Triton X-100 at 0.01%, Complete protease inhibitor cocktail (Roche™, Germany), and DTT 25 mM.

Example 10. Fluorimetric Analysis

About 20 μg of total soluble proteins derived from infected cells, containing different amounts of recombinant GFP protein, were analyzed and quantified by a Tecan™ GENios™ (CA, USA) fluorescence plate reader (excitation [Ex], 485/emission [Em], 535).

Example 11. Western Blot Analysis

Total soluble protein fractions (10 μg) from larvae infected with the recombinant baculoviruses were resolved in 15% SDS-PAGE gels. Gels were stained by the Coomassie blue staining method or transferred to nitrocellulose membranes. Western blots were probed with the anti-GFP monoclonal antibody mab2515 (Millipore™, USA) or tubulin antiserum (T5168; Sigma-Aldrich™) at 1:1000 and the immunocomplexes were revealed with anti-mouse IgG-horseradish peroxidase (HRP)-labeled conjugate (KPL™, UK), diluted 1:2,000 as a secondary antibody. Protein bands were detected using an ECL western blotting detection system and analyzed by the ChemiDoc™ XRS Gel Imaging System (BioRad™, USA).

BIBLIOGRAPHY

1. Nettleship, J. E., Assenberg, R., Diprose, J. M., Rahman-Huq, N., Owens, R. J. Recent advances in the production of proteins in insect and mammalian cells for structural biology. J. Struct. Biol. 2010, 172, 55-65.
2. Gomez-Casado E, Gomez-Sebastian S, Núñez MC, Lasa-Covarrubias R, Martínez-Pulgarin S, Escribano J M. Insect larvae biofactories as a platform for influenza vaccine production. *Protein Expr Purif.* 79: 35-43. 2011.
3. Smith, G. E., M. D. Summers, and M. J. Fraser. 1983. Production of human beta interferon in insect cells infected with a baculovirus expression vector. Mol. *Cell. Biol.* 3: 2156-21 65.
4. Tomita, M., Munetsuna, H., Sato, T., Adachi, T., Hino, R., Hayashi, M., Shimizu, K., Nakamura, N., Tamura, T., Yoshizato, K., 2003. Transgenic silkworms produce recombinant human type III procollagen in cocoons. Nat. Biotechnol. 21 (13, 52-56,
5. Perez-Filgueira, D. M, Resino-Talavan, P., Cubillos, C., Angulo, I., Barderas, M. G., Barcena, J., Escribano, J. M., 2007. Development of a low-cost, insect larvaederived recombinant subunit vaccine against RHDV. Virology 364 (2), 422-430.
6. Perez-Martin, E., Gomez-Sebastian, S., Argilaguet, J. M., Sibila, M., Fort, M., Nofrarias, M., Kurtz, S., Escribano, J. M., Segales, J., Rodriguez, F., 2010. Immunity conferred by an experimental vaccine based on the recombinant PCV2 Cap protein expressed in *Trichoplusia ni*-larvae. Vaccine 28 (11), 2340-2349.
7. Fernández-San Millán A, Gómez-Sebastiàn S, Nuñez MC, Veramendi J, Escribano J M. Human papillomavirus-like particles vaccine efficiently produced in a non-fermentative system based on insect larva. Protein Expr. Purif. 2010, 74: 1-8
8. Gomez-Casado E, Gomez-Sebastian S, Núñez MC, Lasa-Covarrubias R, Martínez-Pulgarín S, Escribano J M. Insect larvae biofactories as a platform for influenza vaccine production Protein Expr. Purif. 2011, 79: 35-43
9. J. A. Medin, L. Hunt, K. Gathy, R. K. Evans, M. S. Coleman, Efficient, low-cost protein factories: expression of human adenosine deaminase in baculovirusinfected insect larvae, Proc. Nati Acad. Sci. USA 87 (1990) 2760-2764.
10. N. M. Tremblay, B. P. Kennedy, I. P. Street, W. J. Kaupp, F. Laliberte, P. K. Weech, Human group II phospholipase A2 expressed in *Trichoplusia ni* larvae-isolation and kinetic properties of the enzyme, Protein Expr. Purif. 4 (1993) 490-498.
11. U. Reis, B. Blum, B. U. von Specht, H. Domdey, J. Collins, Antibody production in silkworm cells and silkworm larvae infected with a dual recombinant *Bombyx mori* nuclear polyhedrosis virus, Biotechnology (NY) 10 (1992) 910-912.
12. F. Gil, M. Perez-Filgueira, M. G. Barderas, C. Pastor-Vargas, C. Alonso, F. Vivanco, J. M. Escribano, Targeting antigens to an invariant epitope of the MHC Class II DR molecule potentiates the immune response to subunit vaccines, Virus Res, (2010).
13. S. Mathavan, V. T. Gautvik, E. Rokkones, O. K. Olstad, B. N. Kareem, S. Maeda, K. M. Gautvik, High-level production of human parathyroid hormone in *Bombyx mori* larvae and BmN cells using recombinant baculovirus, Gene 167 (1995) 33-39.
14. S. Sumathy, V. B. Palhan, K. P. Gopinathan, Expression of human growth hormone in silkworm larvae through recombinant *Bombyx mori* nuclear polyhedrosis virus, Protein Expr. Purif. 7 (1996) 262-268.
15. X. Shi, J. Qin, J. Zhu, D. Zhu, Expression of biologically active human granulocyte-macrophage colony-stimulating factor in the silkworm (*Bombyx mori*), Biotechnol. Appl. Biochem. 24 (Pt 3) (1996) 245-249.
16. M. Q. Pham, S. Naggie, M. Wier, H. J. Cha, W. E. Bentley, Human interleukin-2 production in insect (*Trichoplusia ni*) larvae: effects and partial control of proteolysis, Biotechnol. Bioeng. 62 (1999) 175-182.
17. J. B. Katz, A. L. Shafer, K. A. Eernisse, Construction and insect larval expression of recombinant vesicular stomatitis nucleocapsid protein and its use in competitive ELISA, J. Virol. Methods 54 (1995) 145-157.
18. D. M. Perez-Filgueira, F. Gonzalez-Camacho, C. Gallardo, P. Resino-Talavan, E. Blanco, E. Gomez-Casado, C. Alonso, J. M. Escribano, Optimization and validation of recombinant serological tests for African swine fever diagnosis based on detection of the p30 protein produced in *Trichoplusia ni* larvae, J. Clin. Microbiol. 44 (2006) 3114-3121.
19. S. Gomez-Sebastian, D. M. Perez-Filgueira, E. Gomez-Casado, M. C. Nunez, I. Sanchez-Ramos, E. Tabares, J. M. Escribano, DIVA diagnostic of Aujeszky's disease using an insect-derived virus glycoprotein E, J. Virol, Methods 153 (2008) 29-35.
20. F. Todoli, M. Perez-Filgueira, I. Galindo, S. Gomez-Sebastian, J. M. Escribano, A. Rodriguez-Cortes, J. Alberola, Seroreactivity against raw insect-derived recombinant KMPII, TRYP, and LACK *Leishmania infantum* proteins in infected dogs, Vet. Parasitol. 164 (2009) 154-161.
21. Hill-Perkins M S, Possee R D. A baculovirus expression vector derived from the basic protein promoter of *Autographa californica* nuclear polyhedrosis virus. J Gen Virol. 1990, 71 (Pt 4):971-6.
22. Passareili, A. L., and L. K. Miller. Three baculovirus genes involved in late and very late gene expression: ie-1, ie-n, and lef-2. J. Virol. 1993, 67:2149-2158
23. Rodems, S. M., S. S. Pullen, and P. D. Friesen. DNA-dependent transregulation by IE1 of *Autographa californica* nuclear polyhedrosis virus: IE1 domains required for transactivation and DNA binding. J. Virol. 1997, 71: 9270-9277.
24. Lin X, Chen Y, Yi Y, Zhang Z: Baculovirus immediately early 1, a mediator for homologous regions enhancer function in trans. *Virol J* 2010, 7:32.
25. Okano K, Mikhailov V S, Maeda S: Colocalization of baculovirus IE-1 and two DNA-binding proteins, DBP and LEF-3, to viral replication factories. *Journal of virology* 1999, 73(1):110-119.

The invention claimed is:

1. An insect belonging to the species *Trichoplusia ni* or *Spodoptera frugiperda*, comprising a first nucleic acid sequence introduced into the insect by a recombinant baculovirus wherein the recombinant baculovirus is *Autographa californica* multinuclear polyhedrosis virus (AcMNPV) comprising one copy of an Ac-ie-01 gene in its genome and said first nucleic acid sequence;
wherein said first nucleic acid sequence comprises an extra copy of the Ac-ie-01 gene under control of a promoter and directs expression of immediate early protein-1 (IE-1) or immediate early protein-0 (IE-0) in the insect at levels greater than levels of IE-1 or IE-0 achieved by infecting the insect with a corresponding control baculovirus that comprises one copy of the Ac-ie-01 gene in its genome and does not comprise said first nucleic acid sequence;
wherein said first nucleic acid sequence comprises a nucleic acid sequence selected from the group consisting of:

the nucleic acid sequence of any of SEQ ID NOS:2-5; and the nucleic acid sequence encoding any of the amino acid sequences of SEQ ID NOS: 6-9;

wherein said first nucleic acid further comprises at least one recombinant homologous region (hr) from a baculovirus as enhancer region, wherein said recombinant homologous region (hr) is operably linked to a promoter that drives expression of a recombinant heterologous protein, wherein the promoter is a nucleic acid sequence comprising any of SEQ ID NO: 10-16.

2. The insect according to claim 1, wherein said recombinant homologous region is SEQ ID NO: 27.

3. The insect according to claim 1, wherein the first nucleic acid sequence is selected from the group consisting of SEQ ID NOS: 17, 18, 19, 20, 21, 22, 23, 24, 25 and 26.

4. The insect according to claim 1, further comprising a second nucleic acid sequence encoding a recombinant protein, wherein said second nucleic acid sequence is operably linked to said first nucleic acid sequence, said recombinant homologous region (hr) or said promoter.

5. A method for producing a recombinant protein comprising expressing said recombinant protein in an insect of claim 1 and extracting and purifying said recombinant protein.

6. The method according to claim 5, wherein said recombinant protein is selected from the group consisting of subunit monomeric vaccine, subunit multimeric vaccine, virus like particle, therapeutic protein, antibody, enzyme, cytokine, blood clotting factor, anticoagulant, receptor, hormone and diagnostic protein reagent.

* * * * *

UNITED STATES PATENT AND TRADEMARK OFFICE
CERTIFICATE OF CORRECTION

PATENT NO. : 9,701,983 B2
APPLICATION NO. : 14/407709
DATED : July 11, 2017
INVENTOR(S) : Silvia Gomez Sebastian et al.

It is certified that error appears in the above-identified patent and that said Letters Patent is hereby corrected as shown below:

In the Claims

At Column number 75, Line number 5, delete "wherein said first nucleic acid further comprises at least" and replace it with -- wherein said first nucleic acid sequence further comprises at least --

Signed and Sealed this
Fourteenth Day of November, 2017

Joseph Matal
*Performing the Functions and Duties of the*
*Under Secretary of Commerce for Intellectual Property and*
*Director of the United States Patent and Trademark Office*